United States Patent
Yamaya et al.

[11] Patent Number: 5,860,913
[45] Date of Patent: Jan. 19, 1999

[54] ENDOSCOPE WHOSE DISTAL COVER CAN BE FREELY DETACHABLY ATTACHED TO MAIN DISTAL PART THEREOF WITH HIGH POSITIONING PRECISION

[75] Inventors: Koji Yamaya; Tatsuya Furukawa, both of Hachioji; Takahiro Kishi, Machida; Tsugio Okazaki, Hachioji; Haruhiko Kaiya, Hachioji; Hisao Yabe, Hachioji; Tsutomu Ishiguro, Hachioji, all of Japan

[73] Assignee: Olympus Optical Co., Ltd., Tokyo, Japan

[21] Appl. No.: 848,217

[22] Filed: Apr. 29, 1997

[30] Foreign Application Priority Data

| May 16, 1996 | [JP] | Japan | 8-121746 |
| May 16, 1996 | [JP] | Japan | 8-121748 |
| Feb. 7, 1997 | [JP] | Japan | 9-025592 |
| Feb. 10, 1997 | [JP] | Japan | 9-027002 |

[51] Int. Cl.$^6$ ..................................................... A61B 1/04
[52] U.S. Cl. .......................... 600/127; 600/121; 600/125; 600/129; 600/124
[58] Field of Search ................................. 600/121, 122, 600/123, 124, 125, 127, 129, 134

[56] References Cited

U.S. PATENT DOCUMENTS

| 5,460,166 | 10/1995 | Yabe | 600/121 |
| 5,662,588 | 9/1997 | Iida | 600/127 |
| 5,674,181 | 10/1997 | Iida | 600/127 |

FOREIGN PATENT DOCUMENTS

| 56-8030 | 1/1981 | Japan. |
| 59-181126 | 10/1984 | Japan. |
| 2-25361 | 7/1990 | Japan. |
| 3-46727 | 10/1991 | Japan. |
| 4-314439 | 11/1992 | Japan. |
| 7-184838 | 7/1995 | Japan. |
| 7-323001 | 12/1995 | Japan. |
| 8-19509 | 1/1996 | Japan. |
| 8-243071 | 9/1996 | Japan. |

*Primary Examiner*—Gene Mancene
*Assistant Examiner*—Ira Hatton
*Attorney, Agent, or Firm*—Armstrong, Westerman, Hattori, McLeland & Naughton

[57] ABSTRACT

In an endoscope of the present invention, while a cover indicator on a distal cover is aligned with a scope indicator on a main distal part, the distal cover is put on the main distal part in an axial direction at a certain insertion angle. Thereafter, the distal cover is rotated while being thrust in the axial direction. The stoppage of a locking convex part of a hook of the main distal part by a claw of a reinforcement member is released, and the locking convex part of the hook is positioned in a locking ditch of the reinforcement member. The head of the hook is constrained to move in the axial direction by means of a main distal cover that is an elastic member and the claw. The locking convex part is then fitted into the locking ditch reliably. Consequently, the distal cover can be fixed to the main distal part readily, freely detachably, and reliably with high positioning precision.

28 Claims, 32 Drawing Sheets

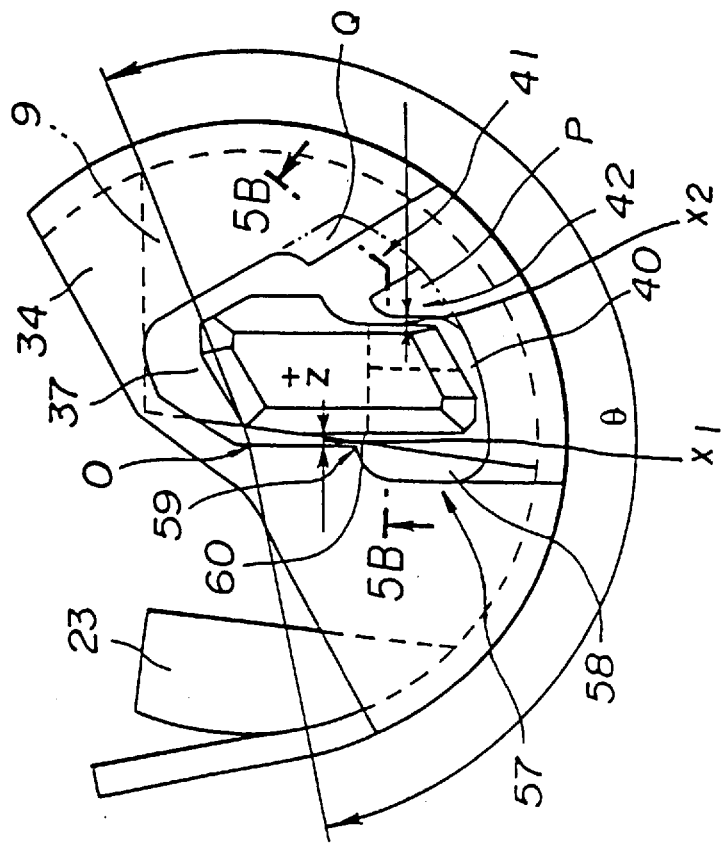

ENDOSCOPE WHOSE DISTAL COVER CAN BE FREELY DETACHABLY ATTACHED TO MAIN DISTAL PART THEREOF WITH HIGH POSITIONING PRECISION

BACKGROUND OF THE INVENTION

1. Field of the Invention

The present invention relates to an endoscope, or more particularly, to an endoscope characterized by a distal cover thereof that is freely detachable from a distal part of an insertion unit.

2. Description of the Related Art

In recent years, endoscopes having an elongated insertion unit have been widely adopted in the fields of medicine and industry. The distal part of the insertion unit is formed with a rigid distal member to which an illuminating means and viewing means are fixed.

When the rigid distal part is inserted into a tortuous body cavity in a human body, if the insertion unit is thrust too forcibly with the rigid distal part in contact with the bent part of the cavity wall, there arises a possibility of injuring the cavity wall with the rigid distal part.

In some endoscopes, a portion on the front side of the distal part is shielded with a distal cover having elasticity in order to prevent the distal part from injuring the cavity wall during insertion.

In another endoscope, a stowage in which a stand used to stand a therapeutic instrument is stowed so that the stand can pivot freely is formed with a distal cover. In particular, when the stand used to stand a therapeutic instrument is stowed, it is necessary to fully clean and sterilize the distal cover after use. The distal cover is therefore often structured to be freely detachable.

For example, in a prior art disclosed in Japanese Unexamined Patent Publication No. 8-19509, a cap similar to a distal cover is fixed to a main distal part by inserting a fixing screw into a screw hole in the main distal part, and then affixed thereto using a sealant. Furthermore, a screw hole larger than the screw hole in the main distal part is bored in the cap. For removing the cap, after the fixing screw is detached, a separation screw is used to push the main distal part in order to separate (detach) the cap affixed to the main distal part using the sealant.

However, in a structure like the structure of the prior art in which the distal cover (cap) is fixed using a screw, a jig such as a driver is needed to attach the distal cover. If the jig is missing, the distal cover cannot be attached. Moreover, the screw is inserted into the distal part and is therefore small in size. The screw is liable to get missing. If the screw gets missing prior to an endoscopic examination, the distal cover cannot be fixed and the examination cannot be started. Moreover, since the screw must be tightened to fix the distal cover, the work is cumbersome. Furthermore, the separation screw is needed to detach the cap.

By the way, a distal cover formed with an elastic member made of a rubber or the like and having a hole into which a convex part of a main distal part is fitted is conceivable as a simple detachable distal cover. This structure has possibilities of not being fixed satisfactorily, being positioned with poor precision, or being displaced or coming off during an examination.

Talking of a known side-looking endoscope, Japanese Unexamined Patent Publication No. 8-243071 has disclosed an endoscope in which a distal cover thereof is made detachable and the efficiency in cleaning the surroundings of a forceps stand is improved. In this endoscope, as shown in FIG. 51, the distal cover is thrust in an axial direction, a jut 503 of a distal part 502 is fitted into a hole 501 in a cover 500, and the cover is fixed using a screw 504. According to this method described in the Japanese Unexamined Patent Publication No. 8-243071, if the screw 504 comes off after the endoscope is inserted into a body cavity, there is no means for recognizing the fact. If the screw 504 comes off within the body cavity and the cover 500 almost comes off, the fact cannot be recognized until the cover 500 drops. This is a critical problem in terms of safety.

In medical-purpose endoscopes including a gastroscope and duodenoscope, an insertion unit of an endoscope is inserted into a patient's body cavity in order to view or treat a lesion. Some medical-purpose endoscopes include a therapeutic instrument standing unit as a mechanism for directing forceps or any other therapeutic instrument toward a desired lesion so as to collect a biomedical tissue or treat the lesion while viewing the lesion.

The therapeutic instrument standing unit basically comprises a therapeutic instrument stand capable of pivoting with a standing axis located in a distal structure as a center, and an operation wire coupled to the therapeutic instrument stand. When an operator advances or withdraws the operation wire by handling an operation unit, the angle of the therapeutic instrument stand is changed to direct the forceps in a desired direction.

When the endoscope is in operation, intracavitary fluid invades into an area in which the standing axis of the therapeutic stand and the distal structure are engaged with each other, or an area in which an operation wire fixing member connected to an end of the operation wire and the therapeutic instrument stand are engaged with each other.

The endoscope must therefore be cleaned (sterilized) after use. It is time-consuming to clean the operation wire fixing member and standing axis. Under the circumstances, Japanese Unexamined Patent Publication No. 7-323001 has proposed an endoscope whose distal cover is easily attachable or detachable to or from a distal structure.

However, in known endoscopes, in which a distal cover is freely detachable from a distal structure, including the endoscope disclosed in the Japanese Unexamined Patent Publication No. 7-323001, a small gap may be created between the distal cover and distal structure. In this state, if a treatment using a high-frequency current is carried out, there arises a possibility that the high-frequency current may leak out to the outer surface of a distal part via intracavitary fluid invading into the gap between the distal cover and distal structure. If the outer surface of the distal part should be in contact with an intracavitary wall, there would arise a possibility that the current flows to the intracavitary wall.

OBJECTS AND SUMMARY OF THE INVENTION

An object of the present invention is to provide an endoscope having a fixing mechanism capable of reliably fixing a distal cover to a distal part in an easily detachable manner with high positioning precision.

Another object of the present invention is to provide an endoscope that if a cover located at the distal part of an insertion unit almost comes off during an endoscopic examination, enables ready recognition of the state.

Yet another object of the present invention is to provide an endoscope which can prevent a high-frequency current from leaking out to the outer surface of the distal part of the endoscope even during a treatment using a high-frequency current and of which distal cover is detachable from a distal structure.

An endoscope of the present invention is an endoscope whose distal cover is freely detachable from a main distal part, wherein: each of the distal cover and main distal part has a locking section to be freely detachably locked with a thrust in an axial direction of the distal cover and with a rotation; and the distal cover also has a constraining means for constraining the distal surface of the locking section of the main distal part to move in the axial direction within at least part of the range of the rotation. Each of the distal cover and main distal part has the locking section to be freely detachably locked with a thrust in the axial direction of the distal cover and with a rotation. The constraining means included in the distal cover constrains the distal surface of the locking section of the main distal part to move in the axial direction within at least part of the range of the rotation. Consequently, the distal cover is reliably fixed to the distal part in an easily detachable manner with high positioning precision.

Other features and advantages of the present invention will be fully apparent from the description below.

BRIEF DESCRIPTION OF THE DRAWINGS

FIGS. 1 to 14B relate to a first embodiment of the present invention;

FIG. 1 is a diagram showing the configuration of an endoscope;

FIG. 2 is a diagram showing the structures of a main distal part and distal cover shown in FIG. 1;

FIG. 3 is a side view showing the lateral surfaces of the main distal part and distal cover shown in FIG. 2;

FIG. 5A is a first explanatory diagram for explaining attachment of the main distal part and distal cover shown in FIG. 2;

FIG. 7 is a third explanatory diagram for explaining attachment of the main distal part and distal cover shown in FIG. 2;

FIG. 9 is a diagram showing the appearances of the main distal part and distal cover shown in FIG. 2 which are attached to each other;

FIG. 10 is a sectional view showing a section of the distal cover in FIG. 8A that is attached imperfectly to the main distal part;

FIG. 11 is a diagram showing an example of an incorrect-combination prevention structure disabling a distal cover from being attached to the main distal part shown in FIG. 8A;

FIG. 12 is a diagram showing the major structure of a first variant of the main distal part and distal cover shown in FIG. 1;

FIG. 14B is a sectional view showing a Z—Z section of FIG. 14A;

FIGS. 16 to 27 relate to a third embodiment of the present invention;

FIG. 16 is a diagram showing the configuration of an endoscope;

FIG. 17 is a diagram showing the structures of a main distal part and distal cover shown in FIG. 16;

FIG. 18 is a sectional view showing a section of the distal portion of the main distal part shown in FIG. 17 to which the distal cover is attached;

FIG. 22 is a sectional view showing the longitudinal section of the main distal part shown in FIG. 17 to which the distal cover is attached;

FIG. 25 is a diagram showing the structure of the major portion of a first variant of the endoscope shown in FIG. 16;

FIG. 26 is a diagram showing the structure of the major portion of a second variant of the endoscope shown in FIG. 16;

FIG. 27 is a diagram showing the structure of the major portion of a third variant of the endoscope shown in FIG. 16;

FIG. 28 is a side view showing the whole of an endoscope of the fourth embodiment of the present invention;

FIG. 29 is a perspective view showing the distal part of an insertion unit with a distal cover removed;

FIG. 30 is a sectional view showing a state in which the distal cover is about to be attached to a main distal part;

FIG. 31 is a sectional view showing a state in which the distal cover is attached to the main distal part;

FIG. 32 is an A—A sectional view of FIG. 30;

FIG. 33 is a B—B sectional view of FIG. 30;

FIG. 34 is a first side view (partly side view) showing the longitudinal section of the distal part with the distal cover attached to the main distal part;

FIG. 35 is a second side view (partly side view) showing the longitudinal section thereof with the distal cover attached to the main distal part;

FIG. 36 is a plan view showing a state in which a distal cover is about to be attached to a main distal part;

FIG. 37 is a plan view showing a state in which the distal cover ia attached to the main distal part;

FIG. 38 is a longitudinal sectional view or partly side view showing the state in which the distal cover is about to be attached to the main distal part;

FIG. 39 is a longitudinal sectional view or partly side view showing the state in which the distal cover is attached to the main distal part;

FIG. 40 is a C—C sectional view of FIG. 37 showing a state in which an insert of the distal cover is engaged with the main distal part;

FIG. 41 is a diagram schematically showing an endoscope;

FIG. 42 is an oblique view for explaining the structure of the distal part of the endoscope;

FIG. 43 is an explanatory diagram showing a main distal part and distal cover constituting the distal part;

FIG. 44 is a diagram for explaining a state in which the distal cover is attached to the main distal part;

FIG. 45 is a diagram showing a means for intensifying the strength of fixing the distal cover to an insulator;

FIG. 46 is a diagram for showing a means making it possible to discern the state of the distal cover attached to the main distal part;

FIG. 47 is a diagram showing a relationship between the main distal part and distal cover;

FIG. 48 is a sectional view for explaining a state in which the distal cover is attached to the main distal part;

FIG. 49 is a sectional view for explaining the state in which the attached state of the distal cover relative to the main distal part is imperfect;

FIG. 50 is a sectional view for explaining another state in which the distal cover is attached to the main distal part (attachment is imperfect)

DESCRIPTION OF THE PREFERRED EMBODIMENTS (First Embodiment)

Figure 1:
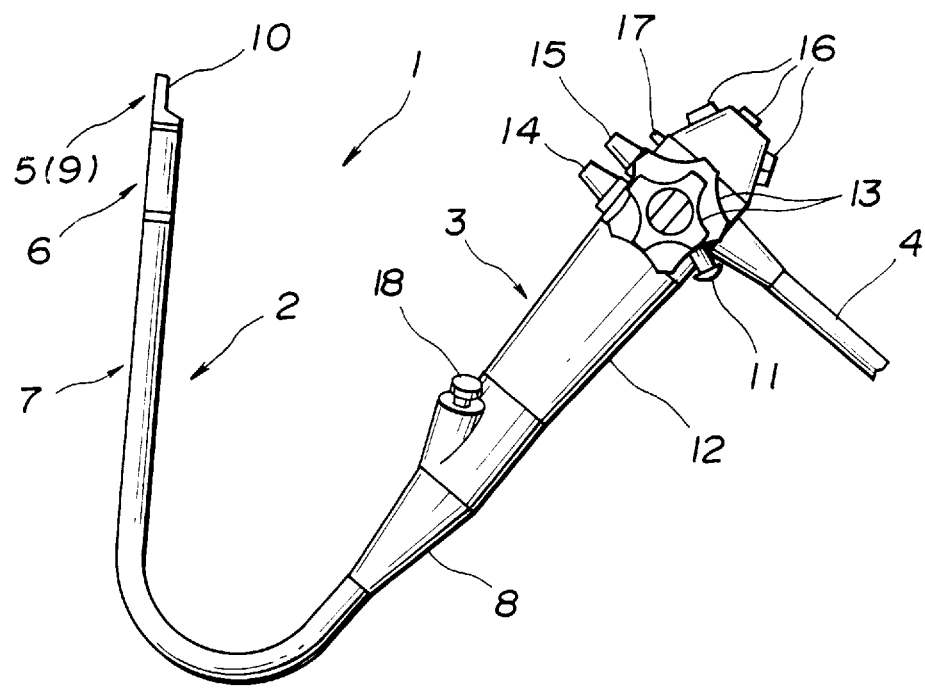

As shown in FIG. 1, an endoscope 1 of a first embodiment of the present invention comprises an elongated insertion unit 2, an operation unit 3 located at the back end of the insertion unit 2, and a universal cord 4 extending laterally from the operation unit 3. The insertion unit 2 has a distal part 5, a bending part 6 that can bend freely, and an elongated flexible part 7 having flexibility in that order from the distal side. A tapered break prevention section 8 is formed as the proximal portion of the flexible part 7. The operation unit 3 communicates with the proximal end of the break prevention section 8.

Figure 2:
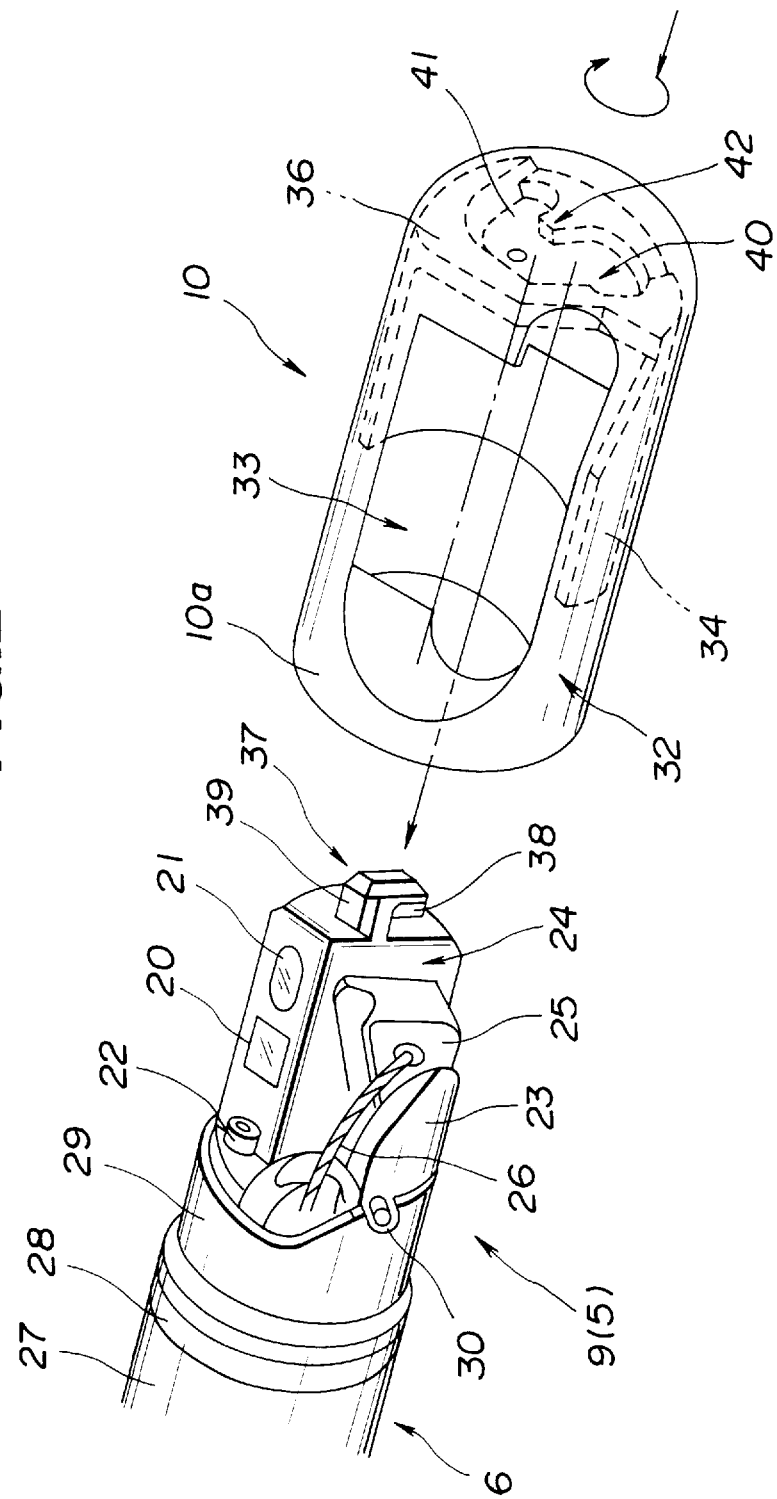

A distal cover 10 is freely detachably attached to a hard main distal part 9 (more particularly, formed with a member made of stainless steel or any other material having rigidity) that is one component of the distal part. FIG. 2 is a diagram showing the distal part 5 of the insertion unit 2 of the endoscope 1 in enlargement, wherein the distal cover 10 is detached from the main distal part 9.

As seen from FIG. 2, an objective lens 20 whose field of view lies in a direction orthogonal to the axial direction (longitudinal direction) of the insertion unit 2, and an illumination lens 21 for emitting illumination light in the direction of the field of view for illumination are located mutually adjacently in the longitudinal direction in the main distal part 9. Moreover, on the proximal side of the main distal part 9, an aeration/perfusion nozzle 22 communicating with an aeration/perfusion channel (not shown) incorporated in the insertion unit 2 is located on the proximal side of the main distal part 9 and directed toward the objective lens 20 for the purpose of supplying a cleaning solvent used to clean the objective lens 20, supplying air used to remove water drops adhering to the objective lens 20, or aerating a body cavity. The main distal part 9 is chamfered at a degree of $CO.2$ or $RO.2$ or higher along the ridge lines on the outer surface thereof. The chamfering facilitates insertion of the distal cover 10 in the axial direction or rotation thereof. Besides, if the distal cover 10 should drop to a body cavity during an examination, the ridge lines on the outer surface of the distal cover 10 would not injure the inside of the body cavity.

An imaging device such as a CCD is located at the position of the image plane of the objective lens 20, though the imaging device is not shown. The imaging device photoelectrically converts a formed image, and transmits an image signal resulting from photoelectric conversion to a video processor or camera control unit connected via the universal cord 4 over a signal cable connected to the imaging device. The video processor or camera control unit carried out signal processing so as to convert the image signal into a standard video signal. Eventually, an endoscopic image formed by the imaging device is displayed on a color monitor that is not shown.

Moreover, the distal surface of a bundle of light guide fibers, which is not shown, is located inside the illumination lens 21 within the main distal part 9. The bundle of light guide fibers runs through the universal cord 4 via the insertion unit 2 and operation unit 3. A light guide connector attached to the terminal of the bundle of light guide fibers is connected to a light source apparatus that is not shown, whereby illumination light supplied from the light source apparatus is transmitted. The illumination light is emitted through the distal surface in the direction of the field of view of the objective lens 20 via the illumination lens 21.

The opposite portion of the main distal part 9 adjoining a semi-cylindrical portion including the aeration/perfusion nozzle 22, objective lens 20, and illumination lens 21 is cut out with a lateral fraction 23 alone left. In a space 24 (an area near the proximal end of the main distal part 9) resulting from the cutout, a therapeutic instrument stand 25 is located with the proximal end thereof supported by the main distal part 9 in a freely pivotable manner. The tip of a standing wire 26 running through the insertion unit 2 is connected to a position near the distal end of the therapeutic instrument stand 25.

The standing wire 26 having one end thereof connected to the therapeutic instrument stand 25 is passed through the insertion unit 2, connected to a standing mechanism incorporated in the operation unit 3. A therapeutic instrument standing lever 11 (See FIG. 1) is connected to the standing mechanism. By turning the therapeutic instrument standing lever 11, the standing wire 26 is pulled and the inclination of the therapeutic instrument stand 25 is changed. Thus, a direction in which the distal end of a therapeutic instrument juts out can be controlled or varied.

Referring back to FIG. 1, a portion of the operation unit 3 proximal to a grip body 12 to be gripped by a user (upper side in FIG. 1) is provided with a bending knob 13 to be handled to bend the bending part 6, the therapeutic instrument standing lever 11, an aeration/perfusion button 14 to be handled for aeration or perfusion, a suction button 15 to be handled for suction, and a plurality of operation switches 16 to be handled to give the video processor or camera control unit instructions concerning image control such as an instruction for instructing display of a still image.

Moreover, the operation unit 3 has a standing wire cleaning base 17 at a position adjoining the suction button 15. The standing wire cleaning base 17 communicates with the proximal end of a standing wire channel (not shown) through which the standing wire 26 runs, and is used to clean the standing wire channel. The proximal end of a therapeutic instrument channel (not shown) incorporated in the insertion unit 2 communicates with a channel insertion port 18 through which a therapeutic instrument can be inserted.

As shown in FIG. 2, the proximal end of the main distal part 9 is connected to a bending tube (not shown) composed of a plurality of bending tops (not shown) constituting the bending part 6. The bending part 6 is shielded with a bending part shielding member 27 that serves as an armour and that is made of an electrically insulating material. An end of the bending part coating member 27 is fixed in a watertight manner to the main distal part 9 using an adhesive or the like. An insulator 29 made of a thermoplastic resin such as PSU, a modified PPO, or PEI, or made of an electrically insulating material such as a ceramic or silicon rubber is placed along the outer circumference of the main distal part 9 distal to a bending part shielding member fixer 29.

A tightening section 10a for elastically tightening the whole outer circumference of the insulator 29 at the time of attachment is formed annularly as the proximal portion of the distal cover 10. Owing to the tightening section 10a, the insulator 29 adheres closely to the proximal portion of the distal cover 10. Even when a treatment using a high-frequency current is carried out, the high-frequency current will not leak out to the outer surface of the distal part of the endoscope. Moreover, the tightening section 10a constrains the distal cover 10 to rotate at the time of detaching the distal cover 10. The distal cover 10 will therefore not come off unexpectedly.

Incidentally, the insulator 29 is formed with a convex curved surface, and a metallic coming-off prevention pin 30 is fixed to an edge on the distal side of the insulator 29 using an adhesive or the like so that it is directed toward the main distal part 9. An adhesive or the like is applied to the head of the pin so that the metal will not be bared (not shown).

Figure 3:
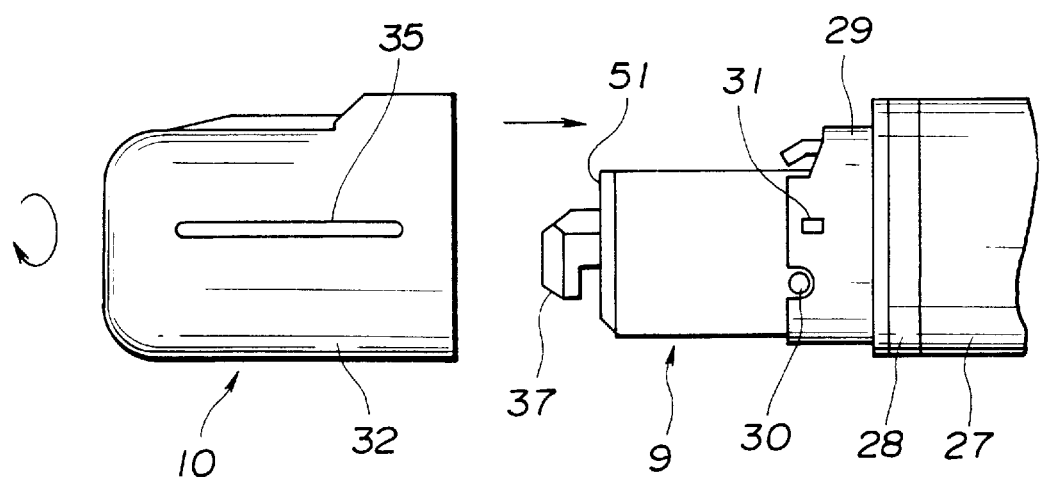

A scope indicator 31 for indicating a position from which the distal cover 10 should be rotated for attachment is, as shown in FIG. 3, formed on the lateral surface of the insulator 29. The scope indicator 31 is formed by applying an adhesive whose color is different from the color of the face of the insulator 29.

Referring back to FIG. 2, a main distal cover 32 forming the distal cover 10 is shaped like a cap so that it can cover the main distal part 9, and has an opening 33 formed on the side on which the opening 33 will coincide with the objective lens 20, illumination lens 21, and therapeutic instrument stand 25.

A reinforcement member 34 is formed as part of a main distal cover 32 inside the distal cover 10 so that it can cover part of the main distal part 9 including the lateral fraction 23. However, the reinforcement member 34 is invisible from the outer surface of the distal cover 10. The process for forming the reinforcement member 34 as part of the main distal cover 32 may be an insert molding process for molding them in one united body, or a process of creating them separately and uniting them using an adhesive or the like.

The main distal cover 32 is made of a rubber composed of electrically insulating materials or of thermoplastic elastomer. On the outer surface of the main distal cover 32, a cover indicator 35 extending parallel to the axial direction of the cover is formed as shown in FIG. 3.

As shown in FIG. 2, the reinforcement member 34 is made of a material having rigidity such as stainless steel or hard plastic, and shaped to have a bottom 36 on the distal side. The inclusion of the bottom 36 leads to the improved rigidity of the distal cover 10. The bottom 36 of the reinforcement member 34 has a shape making it possible to freely detachably fix the distal cover 10 to the main distal part 9.

Figure 4A:
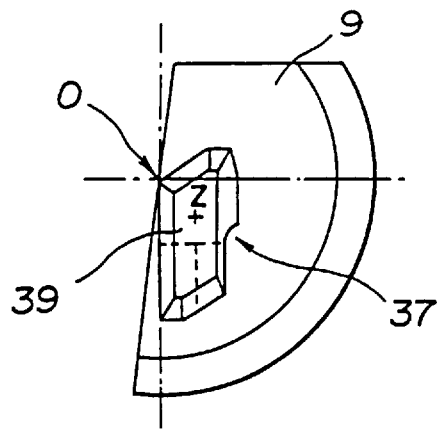
FIG. 4A is a first diagram showing the structure of a hook shown in FIG. 2.
Figure 4B:
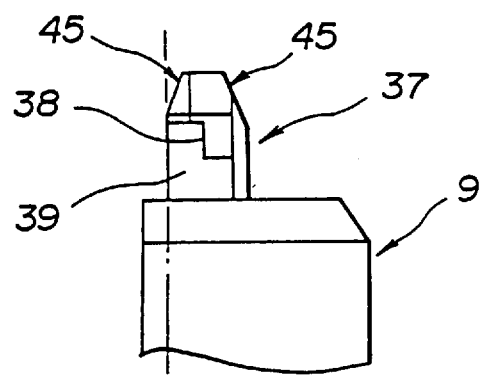
FIG. 4B is a second diagram showing the structure of the hook shown in FIG. 2.

The distal surface of the main distal part 9 has an L-shaped hard hook 37 serving as a locking section for fixing the distal cover 10 freely detachably. FIGS. 4A and 4B are enlarged views of the hook 37. FIG. 4A is a front view, while FIG. 4B is a side view. The hook may have any shape.

As seen from FIG. 4B, the head of the hook 37 is chamfered 45 (or rounded) along substantially the whole circumference. A locking convex part 38 for locking the distal cover 10 is formed on the back of the hook 37. The hook 37 lies on the projective plane in the axial direction of the main distal part 9. The hook 37 is also chamfered at a degree of CO.2 or RO.2, or higher along the ridge lines of the outer surface thereof. As shown in FIG. 4A, the center of a column section 39 of the hook 37, Z, is inconsistent with the center of an outer diameter of the main distal part 9, O. The center O serves as a center of rotation for the distal cover 10 and main distal part 9.

Since the hook 37 lies on the projective plane in the axial direction of the main distal part 9, the hook 37 does not jut out beyond the outer diameter of the main distal part 9. If the distal cover 10 should drop, an intracavitary wall would not be injured during pull-out of the insertion unit 2 from a body cavity, but would be secured. Moreover, since the hook 37 is chamfered at a degree of CO.2 or RO.2, or higher along the ridge lines of the outer surface thereof, the distal cover 10 can readily be inserted in the axial direction or rotated.

The hook 37 may, as shown in FIG. 4A, not be united with the main distal part 9, but may be formed separately and then fixed to the main distal part 9 using a screw or adhesive or by performing welding.

Referring back to FIG. 2, the bottom 36 of the reinforcement member 34 has a hook inserting section 40 in which the hook 37 can be inserted in the axial direction at a certain angle of rotation, and a locking ditch 41 in which the locking convex part 38 of the hook 37 is locked with a one-step thrust and rotation of the distal cover 10.

Furthermore, a convex claw 42 facing the center of rotation of the distal cover 10, O, is formed on the border between the hook inserting section 40 and locking ditch 41 formed in the bottom 36 of the reinforcement member 34. The whole surface on the distal side of the bottom 36 of the reinforcement member 34 having the hook inserting section 40 and locking ditch 41 is covered with the main distal cover 32.

Next, a procedure of attaching the distal cover 9 to the main distal part 8 will be described.

First, as shown in FIG. 3, while the cover indicator 35 is aligned with the scope indicator 31, the distal cover 10 is put on the main distal part 9 in the axial direction at a certain angle of rotation. FIG. 5A is a view showing from the distal side a state after the distal cover 10 is inserted in the axial direction.

As shown in FIG. 5A, in this state, the hook 37 is inserted in the hook inserting section 40 (the main distal cover is not shown). The main distal part 9 and reinforcement member 34 are engaged with each other. An angle θ defined with the engaged circumferential portions is set to a large angle exceeding 180° (ideally, the angle θ is 190° or larger). Assuming that right-hand and left-hand gaps are x1 and x2, a clearance in a horizontal direction that affects a backlash in the direction of rotation between the hook 37 and reinforcement member 34 is x1+x2.

In areas P and Q defined with an alternate long and two short dashes line and a solid line, the main distal cover 32 is not molded in line with the contour of the reinforcement member 34. As apparent from FIG. 5B that is an A—A sectional view of FIG. 5A, there is a space between the reinforcement member 34 and main distal cover 32 in the areas P and Q. As seen from FIG. 5B, when the head of the hook 37 is in contact with the main distal cover 32, a distance from a mounting surface 51 for the hook 37 (See FIG. 3) to the locking convex part 38, L1, and a distance from the mounting surface 51 to a claw abutment surface 52 formed on the distal side of the claw 42, L2, have a relationship of L1<L2. An arrow drawn with a bold line in FIG. 5B indicates a route along which the claw 42 moves at the time of attachment.

In other words, when the head of the hook 37 is in contact with the main distal cover 32, the relationship of L1<L2 is established. In this state, even if the distal cover 10 is rotated clockwise relative to the distal side, the claw 42 acts as a stopper and prevents the locking convex part 38 of the hook 37 from fitting in the locking ditch 41 of the reinforcement member 34.

Figure 5B:
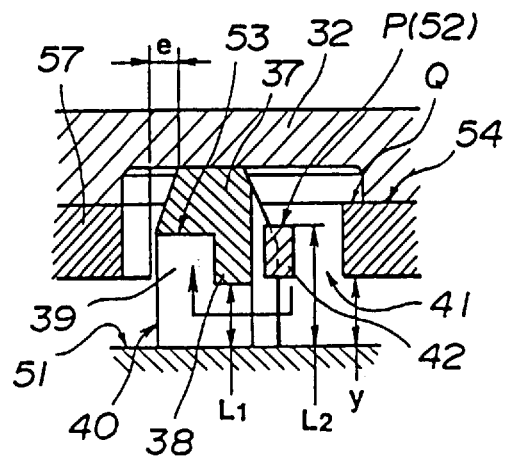
FIG. 5B is a sectional view showing an A—A section of FIG. 5A.
Figure 6A:
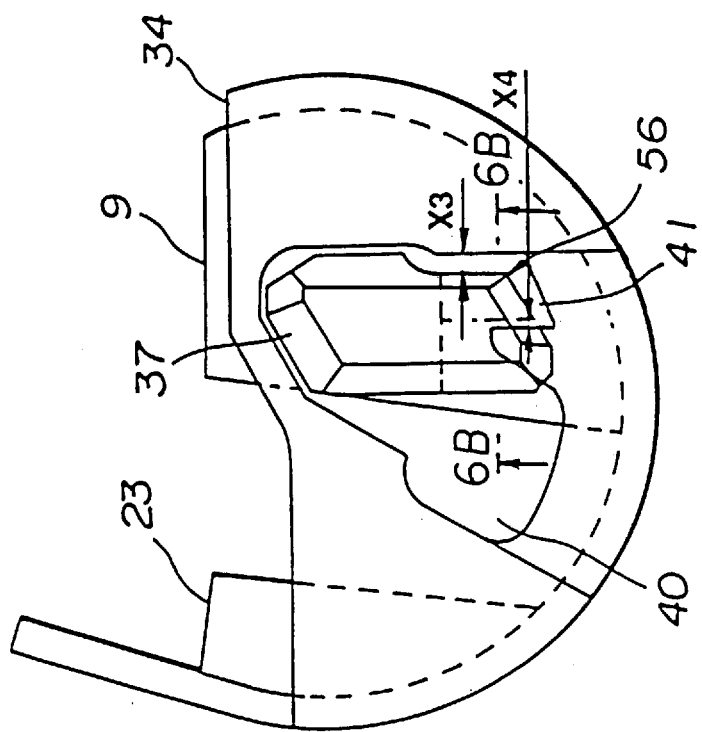
FIG. 6A is a second explanatory diagram for explaining attachment of the main distal part and distal cover shown in FIG. 2.

FIG. 6A shows an attachment-completed state in which the distal cover 10 placed in the state of FIG. 5A is thrust in the axial direction, and then rotated clockwise relative to the distal side so that the locking convex part 38 of the hook 36 is fitted in the locking ditch 41 (the main distal cover is not shown).

In other words, in the state shown in FIG. 6A, positioning in the direction of rotation and in the axial direction is completed. Even in this state, there is a slight backlash in the direction of rotation. A clearance in the horizontal direction resulting in the backlash is x3+x4 where x3 and x4 are right-hand and left-hand gaps in the drawing. Herein, x1+x2>x3+x4 is established. That is to say, the backlash in the direction of rotation is set to become smaller after attachment. Prior to a rotation, since the clearance is large, the hook 37 can be inserted in the hook inserting section 40 easily. After the rotation, since the clearance becomes smaller, the distal cover 10 can be positioned exactly in the distal cover 9.

Figure 6B:
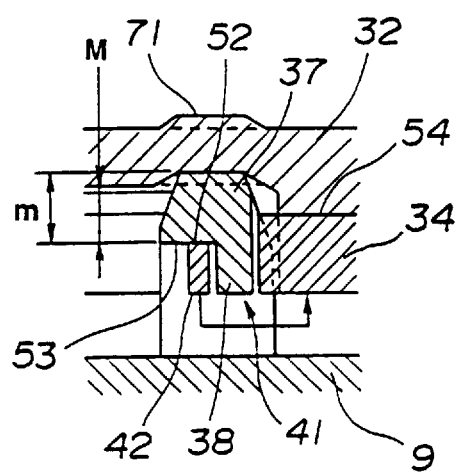
FIG. 6B is a sectional view showing a B—B section of FIG. 6A.

As shown in FIG. 6B that is a B—B sectional view of FIG. 6A, assuming that a distance from the claw abutment surface 52 to the main distal cover 32 is M and a distance from an abutment surface 53 to the head of the hook is m, the distances are set to have a relationship of M<m. Since M<m is established, when attachment is completed, as shown in FIG. 6B, the head of the hook is constrained to move in the axial direction by means of the main distal cover 32 formed with an elastic member and the claw 42. The locking convex part 38 of the hook 37 is therefore fitted firmly in the locking ditch 41, whereby the hook 37 will not come off unexpectedly. Safety is thus guaranteed. An arrow drawn with a bold line in FIG. 6B indicates a route along which the claw 42 moves at the time of detachment.

Referring back to FIG. 5B, the head of the hook 37 is chamfered along substantially the whole circumference thereof. Assuming that a distance from a border 54 between the reinforcement member 34 and main distal cover 32 to the distal surface of the head of the hook 37 is e, the distance e can be set to a large value along the whole circumference of the head owing to the large magnitude of the chamfering.

The distance e is set to have the following relationship with a stroke max in thrusting the distal cover 10 in the axial direction, that is, a distance y in FIG. 5B:

e>y/4

That is to say, since the distance e is set in this way, the reinforcement member 34 and main distal cover 32 on the border 54 will hardly peel off. The reason why the space is preserved in the area Q in FIG. 5A is to ensure a sufficient distance to a pressed surface and thus exert the same effect as the foregoing one.

Figure 7:
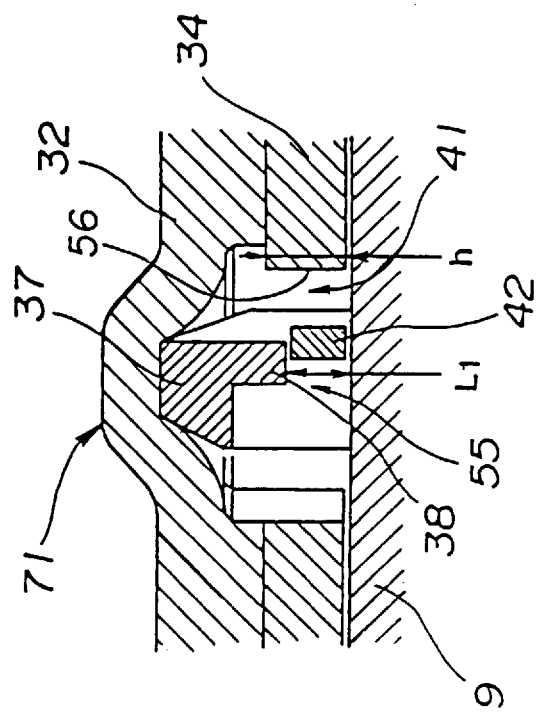

FIG. 7 shows a state attained between the state shown in FIG. 5B and the state shown in FIG. 6B, wherein the claw 42 is passing through a slit 55 on the back side of the hook 37.

As shown in FIG. 7, the height of a lateral wall 56 of the locking ditch of the reinforcement member 34, h, is set to have a relationship h>L1. Since h>L1, the locking convex part 38 of the hook 37 will not ride on the lateral wall 56 of the locking ditch. The lateral wall 56 acts as a stopper for rotation.

As shown in FIG. 5A, a notch 58 is formed on part of a lateral wall 57 of the hook inserting section of the reinforcement member 34. An edge 59 of the notch 58 is located toward the center of rotation, O with respect to an end 60 of the column section of the hook 37. If the distal cover 10 is rotated fully counterclockwise relative to the tip of the distal cover 10, the edge 59 will first hit the column section 39 of the hook 37 and thus act as a stopper for rotation.

Furthermore, owing to the notch 58, the abutment surface 53 will not ride on the side wall 57 of the hook inserting section.

For detaching the distal cover 10, the foregoing procedure is reversed. The tip of the distal cover 10 is once thrust in the axial direction, and then the locking convex part 38 of the hook 37 is removed from the locking ditch 41. Thereafter, the distal cover 10 is rotated counterclockwise relative to the tip thereof until the hook 37 moves to the hook inserting section 40. Thereafter, the distal cover 10 is pulled forward in the axial direction and thus detached.

For detaching the distal cover 10, a rotation is made counterclockwise relative to the tip of the distal cover 10. In the layout (See FIG. 2) of this embodiment, the objective lens 21 has the field of view blocked when the distal cover 10 is rotated in that direction. This means that when the distal cover 10 is detached, part of the distal cover 10 enters the field of view without fail. If the distal cover 10 should almost come off within a body cavity, an operator will be aware of the fact soon. The body cavity is therefore secured.

Figure 8A:
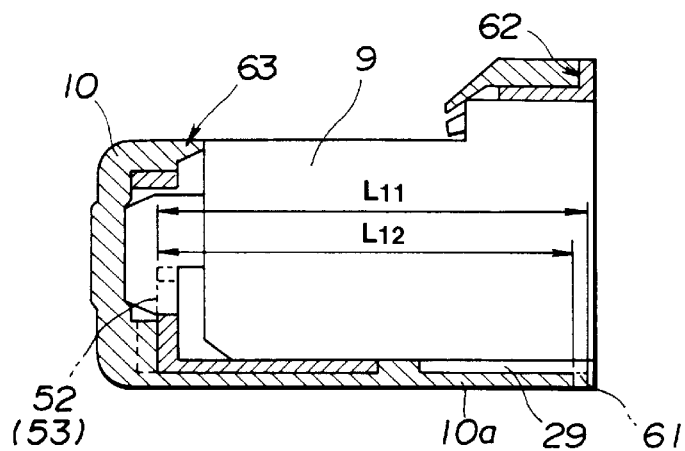
FIG. 8A is a first sectional view showing a section of the distal cover attached to the distal part shown in FIG. 2.

The annular tightening section 10a that is the proximal portion of the distal cover 10 tightens the insulator 29 along the whole outer circumference of the insulator. As shown in FIG. 8A, when the distal cover 10 is in a natural state before attachment, a distance from an end surface 61 on the proximal side to an abutment surface 52 of the claw, L11, and a distance from a hit surface 52 of the insulator hit by the end surface 61 on the proximal side of the distal cover 10 to the abutment surface 53 of the hook, L12 are set to have a relationship L11>L12. Since L11>L12 is established, the distal cover 10 is constrained to move in the axial direction at the time of attachment. Since the distal cover 10 is constrained to move toward the distal side, the locking convex part 38 of the hook 37 is firmly fitted in the locking ditch 41. The distal cover 10 will therefore not come off unexpectedly. Thus, safety is guaranteed.

The distal portion of the distal cover 10 may be provided with a convex elastically-deforming section 63 that deforms when the distal cover 10 is thrust in the axial direction. In an attached state, the tip of the elastically-deforming section 63 and the main distal part 9 (that is, the hook 37) are substantially in contact with each other.

Figure 8B:
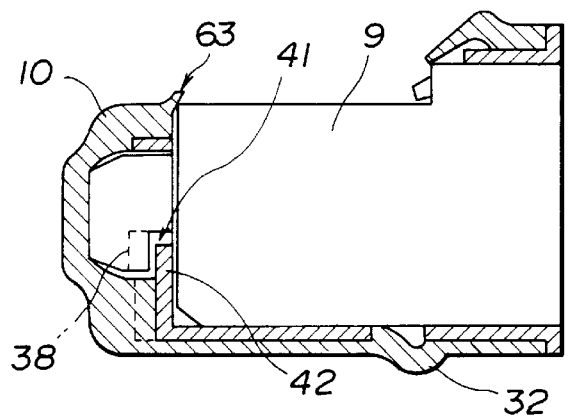
FIG. 8B is a second sectional view showing a section of the distal cover attached to the distal part shown in FIG. 2.

In this state, when the distal cover 10 is thrust in the axial direction in order to detach it, as shown in FIG. 8B, the locking convex part 38 parts from the locking ditch 41 and the elastically-deforming section 63 deforms. At this time, part of the main distal cover 32 deforms as shown in FIG. 8B. In this state, when the thrust in the axial direction is ceased, the main distal cover 32 returns to the state shown in FIG. 8A owing to the restoration force thereof. The distal cover will therefore not come off readily.

Figure 9:
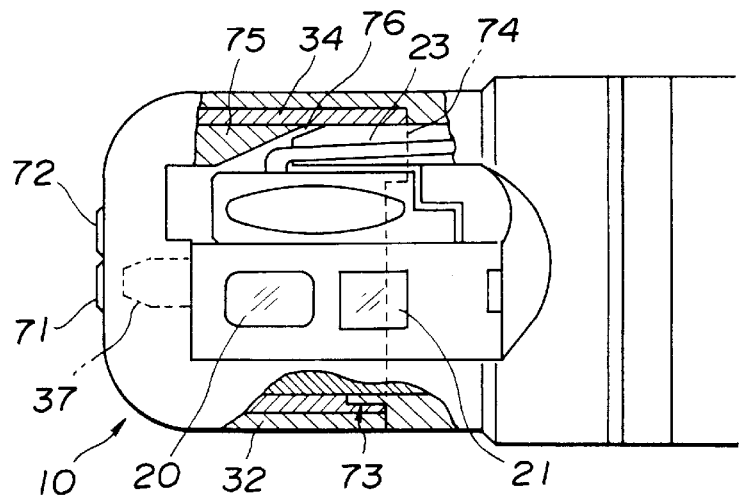

As mentioned above, the main distal cover 32 is formed with an elastic member made of a rubber or thermoplastic elastomer. The head of the hook is constrained by the main distal cover 32 formed with an elastic member and the claw 42. A boss 71 is therefore, as shown in FIG. 9, formed on the outer surface of the distal cover 10. A boss dummy 72 is formed at the tip of the distal cover 10 in advance, thus making the boss 71 indiscernible.

Moreover, the inside of a corner 73 on the proximal side of the reinforcement member 34 is partly notched, and the notched portion is covered by the main distal cover 32. This helps prevent the corner 73 on the proximal side from peeling off.

An extension 74 that is a portion on the proximal side of the reinforcement member 34 is extending in the axial direction so as to meet the lateral fraction 23 of the therapeutic instrument stand 25. Thus, the length in the axial direction by which the reinforcement member 34 meets the lateral fraction 23 with a rotation made to attach or detach the distal cover 10 gets larger. This facilitates rotation. Moreover, an effect of reinforcing the main distal cover 32 over the therapeutic instrument stand 25 is exerted.

Furthermore, a recess 76 used to avoid interference with a therapeutic instrument introduction wall 75 formed on the inside of the main distal cover 32 is preserved beside the lateral fraction 23. Even when a rotation is made to attach or detach the distal cover 10, no interference occurs. Handling is therefore easy.

Figure 10:
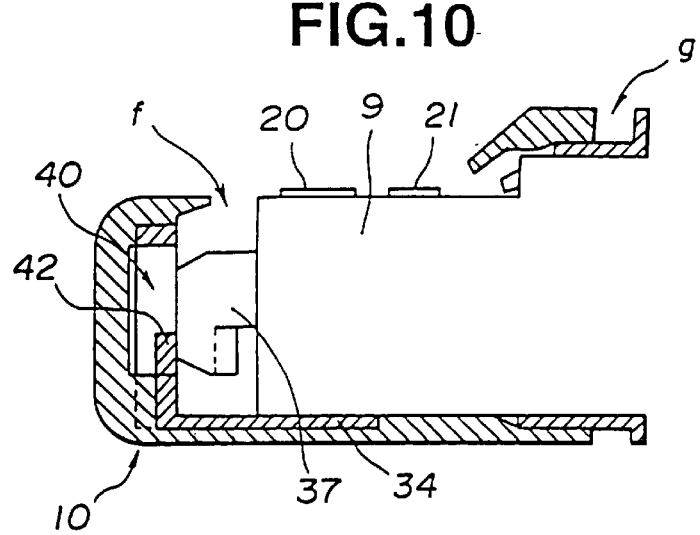

FIG. 10 is a diagram showing a state in which the distal cover 10 is rotated with the hook 37 not inserted in the hook inserting section 40 because of imperfect attachment, and the opening 33 is matched with a portion including the objective lens 21.

In this state, gaps f and g of about 1 mm wide that is clearly visible are preserved back and forth. Thus, it is easily recognizable whether or not the distal cover is attached reliably.

Figure 11:
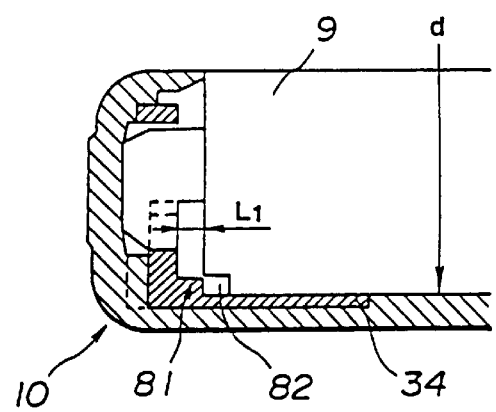

FIG. 11 shows an example of an incorrect-combination prevention structure for disabling the distal cover 10 of another model from being combined incorrectly with the main distal part shown in FIG. 8A.

As shown in FIG. 11, a convex part 81 is formed as part of the bottom 35 of the reinforcement member 34, and a concave part 82 in which the convex part is fitted rotatably is formed in the main distal part 9 along the whole circumference of the main distal part 9.

As long as the distal cover 10 shown in FIG. 11 has the same components as the one shown in FIG. 10 except the foregoing component, the distal cover 10 shown in FIG. 11 will not be combined with the main distal part 9 shown in FIG. 10 because of the convex part 81. The relationship between the concave and convex parts may be reversed, whereas the same effect can be exerted.

The other incorrect-combination prevention structures include an incorrect-combination prevention structure in which the position in the coordinate system at which the hook 37 is mounted may be varied depending on a model, or an incorrect-combination prevention structure in which the diameter of a portion of the reinforcement member 34 which engages circumferentially with the main distal part 9, d, is varied depending on a model. Otherwise, an incorrect-combination prevention structure may be realized by varying the shape of the hook 34 or hook inserting section 39 depending on a model, or by varying the distance L1 on the back side of the hook 36 depending on a model.

In this embodiment, while the cover indicator 35 is aligned with the scope indicator 31, the distal cover 10 is put on the main distal part 9 in the axial direction at a certain angle. Thereafter, the distal cover 10 is rotated while being thrust in the axial direction, whereby the stoppage of the locking convex part 38 of the hook 37 by the claw 42 is released. The locking convex part 38 of the hook 37 is then positioned in the locking ditch 41 of the reinforcement member 34, and the head of the hook 37 is constrained in the axial direction by means of the main distal cover 32 formed with an elastic member and the claw 42. The locking convex part 38 is thus reliably fitted in the locking ditch 41. Consequently, the distal cover 10 can be reliably fixed to the main distal part 9 in an easily detachable manner with high positioning precision.

Figure 12:
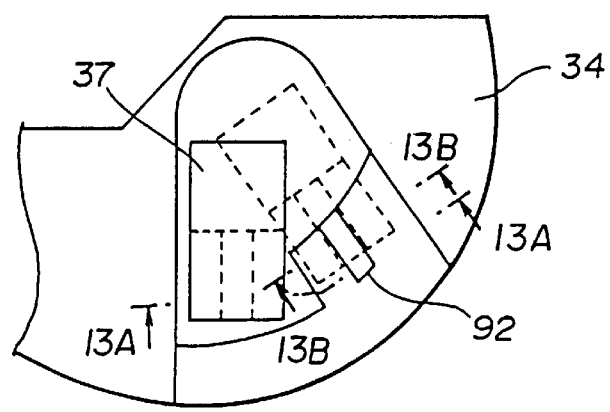

In a first variant of this embodiment, as shown in FIG. 12, the relationship between the convex and concave parts is reversed. That is to say, a second concave part 91 (See FIGS. 13A and 13B) may be formed on the back side of the hook 37, and a second convex part 92 may be formed on the reinforcement member 34.

Figure 13A:
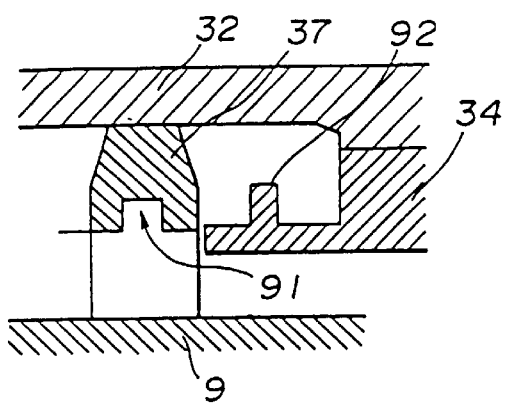
FIG. 13A is a sectional view showing an X—X section of FIG. 12.
Figure 13B:
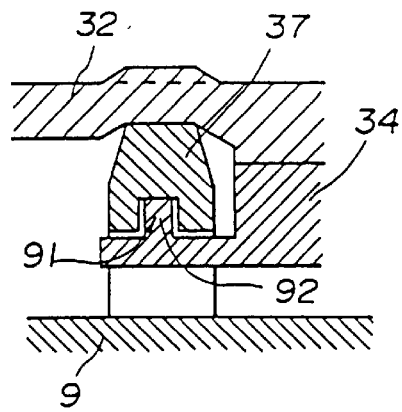
FIG. 13B is a sectional view showing a Y—Y section of FIG. 12.

In this case, the second concave part 91 and second convex part 92 placed in the state of FIG. 13A are, similarly to those in this embodiment, engaged with each other as shown in FIG. 13B with a one-step thrust and rotation (clockwise rotation relative to the distal side) of the distal cover 10. In the first variant, similarly to the first embodiment, the distal cover 10 can be freely detachably fixed to the main distal part 9 readily and reliably. Restrictions on rotation and movement in the axial direction are imposed reliably. For detachment, the distal cover must be thrust once toward the root of the hook 37 and then rotated. The distal cover will therefore hardly come off in a body cavity.

Figure 14A:
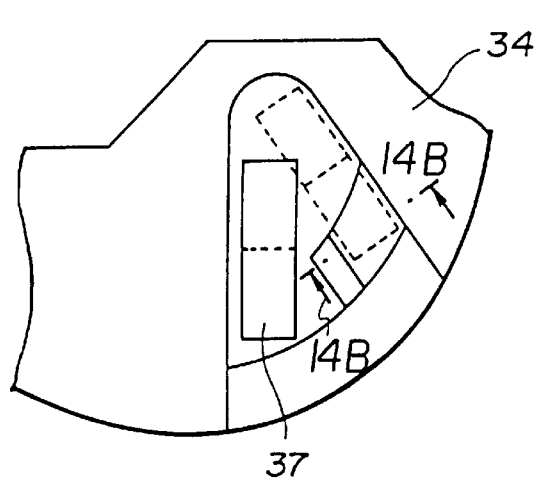
FIG. 14A is a diagram showing the major structure of a second variant of the main distal part and distal cover shown in FIG. 1.
Figure 14B:
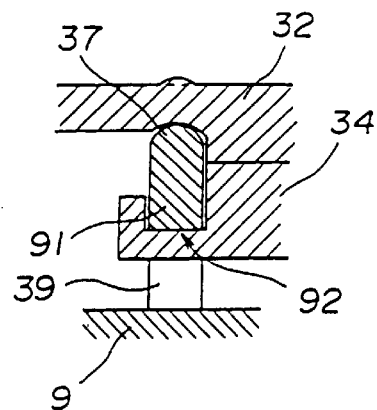

In a second variant of this embodiment, as shown in FIG. 14A, when the distal cover 10 is inserted in the axial direction, the hook 37 is located at a position indicated with a solid line delineating the contour thereof. After the distal cover 10 is thrust in the axial direction, when the distal cover 10 is rotated, the hook is located at a position indicated with a dotted line delineating the counter thereof (the main distal cover 32 is not shown). Specifically, as shown in FIG. 14B that is a Z—Z sectional view of FIG. 14A, a mouth section 91 of the hook 37 is freely detachably fitted in a third concave part 92 of the reinforcement member 34 with the same handling as that in this embodiment. Even this variant can exert the same operation and effect as the first embodiment.

(Second Embodiment)

Figure 15:
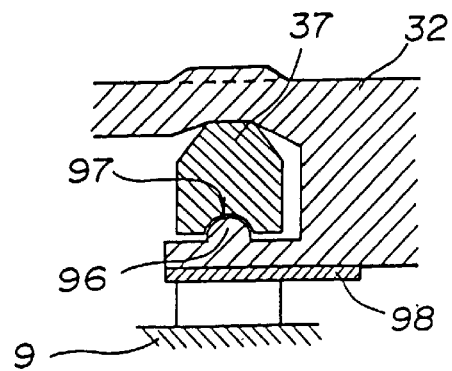
FIG. 15 is an explanatory diagram for explaining attachment of a main distal part and distal cover in accordance with a second embodiment of the present invention.

The first embodiment includes a structure for locking the hook 37 in the reinforcement member 34. In this embodiment, a structure for locking the distal cover 10 in the main distal cover 32 is included. As shown in FIG. 15, the hook 37 has a fourth concave part 97, and the main distal cover 32 has a fourth convex part 96 therein. A reinforcement plate 98 is placed on the back of the fourth convex part 96, thus reinforcing the locking structure.

In this embodiment, the reinforcement member 34 in the first embodiment is excluded. The main distal cover 32 is therefore in contact with the main distal part 9 over substantially the whole length of the main distal cover. The other components are identical to those in the first embodiment.

With the above components, even this embodiment can exert the same operation and effect as the first embodiment.

The fourth convex part 96 is shaped like a semi-circle, the fourth convex part 96 can be engaged with or disengaged from the fourth concave part 97 with a rotation alone without any intentional thrush in the axial direction. The shape may not be a semi-circle but may be a slope.

(Third Embodiment)

Figure 16:
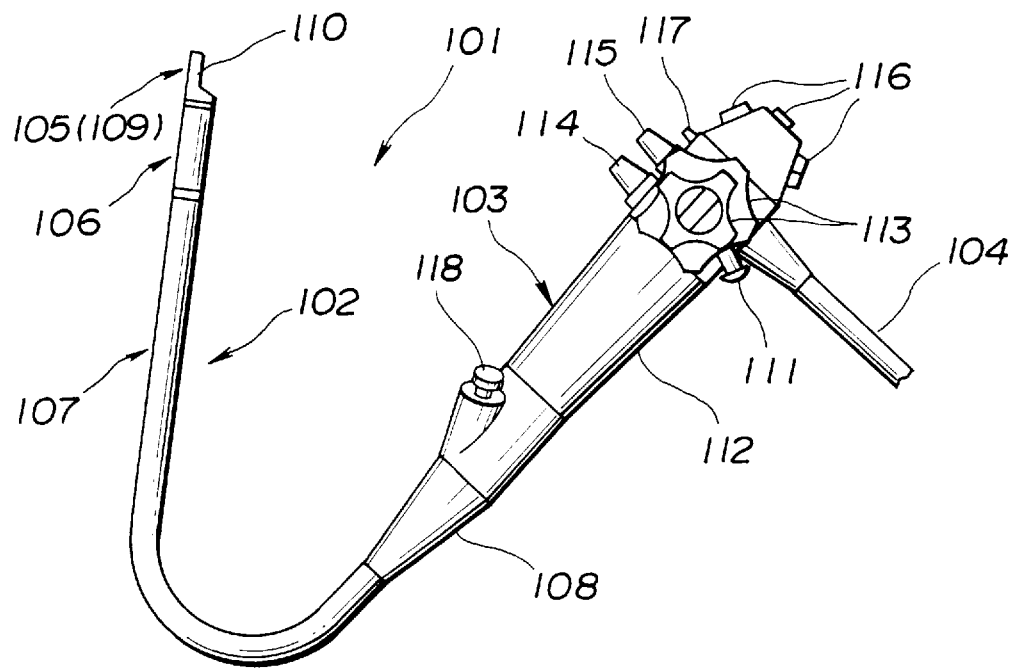

As shown in FIG. 16, an endoscope 101 of this embodiment comprises an elongated insertion unit 102, an operation unit 103 located at the back end of the insertion unit 102, and a universal cord 104 extending laterally from the operation unit 103. The insertion unit 102 has a distal part 105, a bending part 106 that can bend freely, an elongated flexible part 107 having flexibility in that order from the distal side. A tapered break prevention section 108 is formed as the proximal portion of the flexible part 107. The operation unit 103 is coupled to the proximal end of the break prevention section 108.

A distal cover 110 is freely detachably attached to a hard main distal part 109 (more particularly, formed with a member made of a material having rigidity such as stainless steel) constituting the distal part 105 with a rotation.

Figure 17:
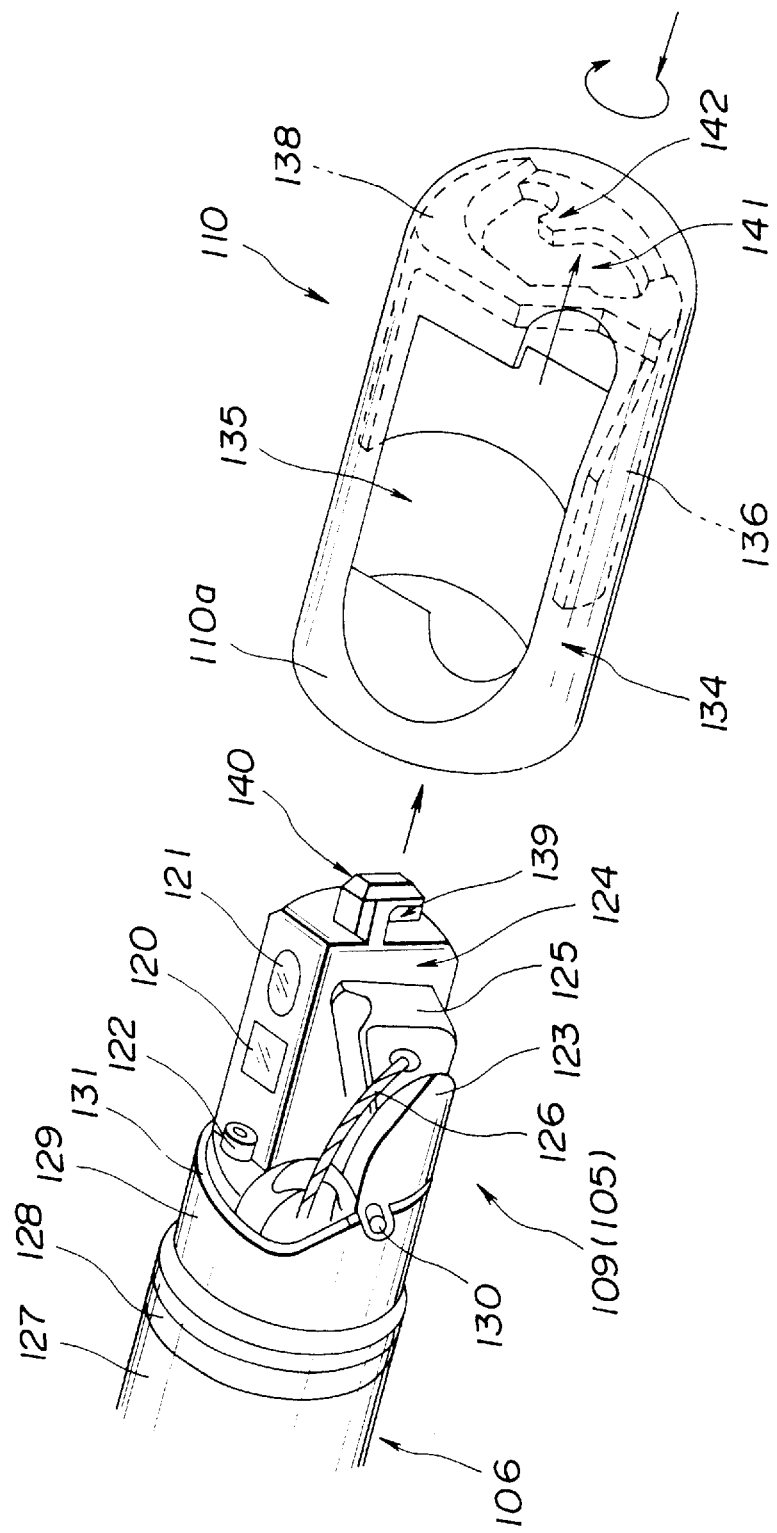

As shown in FIG. 17, in the main distal part 109, an objective lens 120 whose field of view lies in a direction orthogonal to the axial (longitudinal) direction of the insertion unit 102, and an illumination lens 121 for emitting illumination light in the direction of the field of view for illumination are included mutually adjacently in the longitudinal direction. Moreover, an aeration/perfusion nozzle 122 communicating with an aeration/perfusion channel (not shown) incorporated in the insertion unit 102 is located on the proximal side of the main distal part 109 and directed toward the objective lens 120 for the purpose of supplying a cleaning solvent used to clean the objective lens 120, supplying air used to remove water drops adhering to the objective lens 120, or aerating a body cavity.

Figure 18:
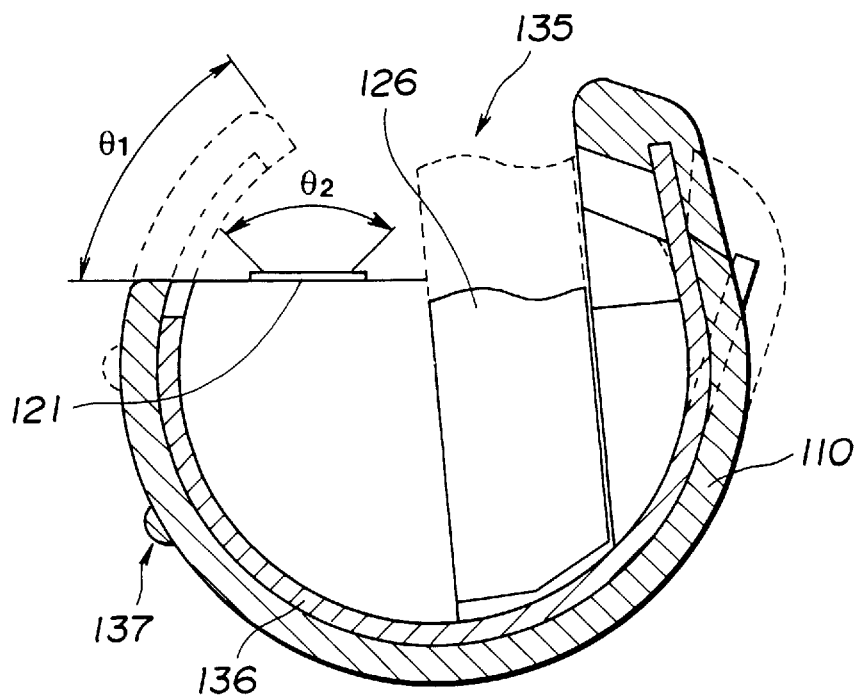

When the main distal part 109 and distal cover 110 are attached to each other with a rotation, the range of rotating the distal cover 110 is, as shown in FIG. 18, defined with an angle θ1. By contrast, the range of the field of view of the objective optical system including the objective lens 120 is defined with an angle θ2. When the distal cover 110 is detached from the main distal part 109, the edge of the distal cover 110 enters the range of the angle θ2 without fail.

An imaging device such as a CCD is located at the position of the image plane of the objective lens 120, though the imaging device is not illustrated. The imaging device photoelectrically converts a formed image, and transmits an image signal resulting from the photoelectric conversion to a video processor or camera control unit connected by way of the universal cord 104 over a signal cable connected to the imaging device. The video processor or camera control unit then carries out signal processing to convert the signal into a standard video signal, and then displays an endoscopic image formed by the imaging device on a color monitor that is not shown.

The distal surface of a bundle of light guide fibers, which is not shown, is located inside the illumination lens 121 in the main distal part 109. The bundle of light guide fibers runs through the universal cord 104 via the insertion unit 102 and operation unit 103. When a light guide connector formed at a terminal of the bundle of light guide fibers is connected to a light source apparatus that is not shown, illumination light supplied from the light source apparatus is transmitted, and emitted through the distal surface in the direction of the field of view of the objective lens 120 via the illumination lens 121.

As shown in FIG. 17, the opposite portion of the main distal part 109 adjoining a semi-cylindrical portion having the aeration/perfusion nozzle 122, objective lens 120, and illumination lens 121 is cut out with only a lateral fraction 123 left intact. In the space 124 created by the cutout (in an area near the proximal end of the main distal part 109), a therapeutic instrument stand 125 is located with the proximal end thereof supported by the main distal part 109 in a freely pivotable manner. The tip of a standing wire 126 running through the insertion unit 102 is connected to a position near the distal end of the therapeutic instrument stand 125. An area in the space 124 on the distal side is used to attach or detach the distal cover 110 (more particularly, used as a space in which the distal cover 110 is tilted for attachment or detachment).

The standing wire 126 having one end thereof connected to the therapeutic instrument stand 125 is passed through the insertion unit 102, and connected to a standing mechanism incorporated in the operation unit 103. A therapeutic instrument standing lever 111 (See FIG. 16) is connected to the standing mechanism. When the therapeutic instrument standing lever 111 is handled to be turned, the standing wire 126 is pulled and the inclination of the therapeutic instrument stand 125 is changed. Thus, a direction in which the tip of a therapeutic instrument juts out can be controlled or varied.

Referring back to FIG. 16, the operation unit 103 has, in a portion thereof proximal to a grip body 112 to be gripped by a user, a bending knob 113 used to bend the bending part 106, the therapeutic instrument standing lever 111, an aeration/perfusion button 114 used for aeration or perfusion, a suction button 115 used for suction, and a plurality of operation switches 116 used to give instructions concerning image control including an instruction for instructing display of a still image to the video processor or camera control unit.

A standing wire cleaning base 117 is located at a position adjacent to the suction button 115 on the operation unit 103. The standing wire cleaning base 117 communicates with the proximal end of a standing wire channel (not shown) through which the standing wire 126 runs, and is used to clean the standing wire channel. The proximal end of a therapeutic instrument channel (not shown) incorporated in the insertion unit 102 communicates with a channel insertion port 118. A therapeutic instrument can be inserted through the channel insertion port 118.

As shown in FIG. 17, the proximal end of the main distal part 109 is connected to a bending tube (not shown) composed of a plurality of bending tops (not shown) constituting the bending part 106. The bending part 106 is shielded by a bending part shielding member 127 that serves as an armour and that is made of an electrically insulating material. An end of the bending part shielding member 127 is fixed to the main distal part 109 in a watertight manner using an adhesive or the like. An insulator 129 made of a thermoplastic resin such as PSU, a modified PPO, or PEI, or made of an electrically insulating material such as a ceramic or silicon rubber is placed over the outer circumference of the main distal part 109 distal to a bending part shielding member fixer 128. A tightening section 110a for elastically tightening the insulator 129 along the whole outer circumference of the insulator 129 at the time of attachment is formed annularly as the proximal portion of the distal cover 110.

A metallic coming-off prevention pin 130 is fixed to an edge on the distal side of the insulator 129 using an adhesive in such a way that the pin 130 is directed toward the main distal part 109. An adhesive 131 is applied to the head of the pin 130 so that the metal will not be bared. The adhesive 131 is, as shown in FIG. 19A, applied in such a way that the insulator 129 and main distal part 109 are linked with a moderate sloop without any gap.

Figure 20A:
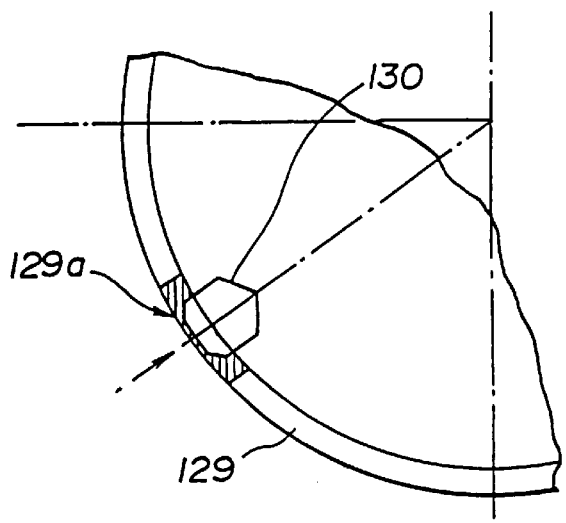
FIG. 20A is an explanatory diagram for explaining the state of a coming-off prevention pin shown in FIG. 17 relative to a notch.
Figure 20B:
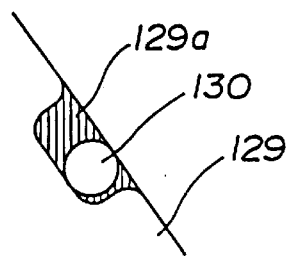
FIG. 20B is an arrow-A view of FIG. 20A showing the state of the coming-off prevention pin relative to the notch.

For fixing the coming-off prevention pin 130, as shown in FIG. 20A, a notch 129a is formed in the lateral surface of the insulator 129. The width of the notch 129a is larger than the diameter of the coming-off prevention pin 130 as shown in FIG. 20B that is a view showing the state of FIG. 20A in a direction of an arrow A. The coming-off prevention pin 130 can be located at any position within the range of the width of the notch 129a. When the endoscope is designed to share parts with another endoscope, restrictions to be imposed on the position of the coming-off pin 130 are alleviated.

Figure 19A:
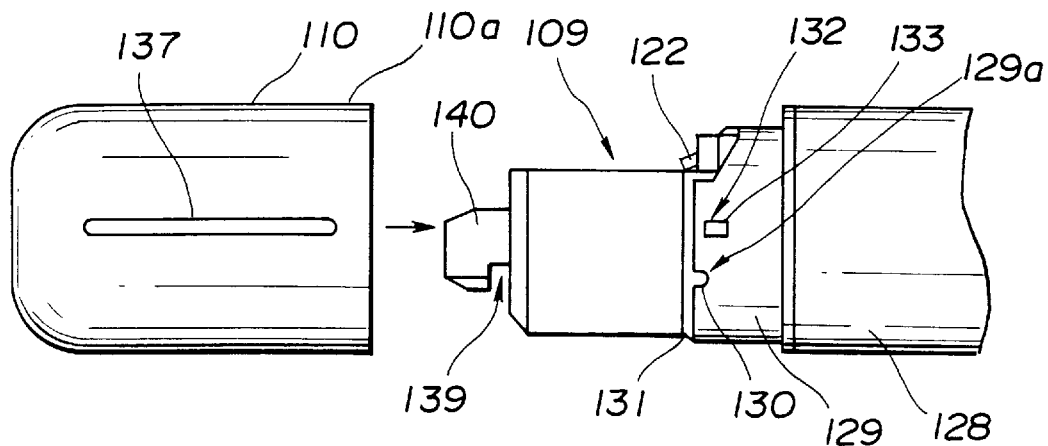
FIG. 19A is a first explanatory diagram for explaining attachment of the main distal part and distal cover shown in FIG. 17.

By the way, as shown in FIG. 19A, a scope indicator 132 indicating a position from which the distal cover 110 should be rotated for attachment is formed on the lateral surface of the insulator 129. The scope indicator 132 is created by applying an adhesive whose color is different from that of the face of the insulator 129. The scope indicator 132 may be produced as, for example, described below.

That is to say, a hole 133 is bored in the insulator 129 in advance, and the insulator 129 is fixed to the main distal part 109 using the adhesive 131. The adhesive 131 has a different color from the insulator 129. The adhesive 131 oozing out of the hole 133 is wiped out. An adhesive 120 remaining inside the hole 133 serves as the scope indicator 132.

Referring back to FIG. 17, the main distal cover 134 constituting the distal cover 110 is shaped like a cap for shielding the main distal part 109, and has an opening 135 on the side on which the opening 135 will coincide with the objective lens 120, illumination lens 121, and therapeutic instrument stand 125.

A reinforcement member 136 is formed inside the distal cover 110 as part of the main distal cover 134 so that the reinforcement member 136 can cover part of the main distal part 109 including the lateral fraction 123. However, the reinforcement member 136 is exposed to the outer surface of the distal cover 110. The process for forming the reinforcement member as part of the main distal cover may be an insert molding process for molding them in one united body or a process of creating them separately and then uniting them using an adhesive or the like.

The main distal cover 134 is made of a rubber or thermoplastic elastomer, and has, as shown in FIG. 19A, a cover indicator 137 extending parallel to the axial direction of the distal cover 110 on the outer surface thereof.

As shown in FIG. 17, the reinforcement member 136 is made of a material having rigidity such as stainless steel or hard plastic, and shaped to have a bottom 138 on the distal side. The presence of the bottom 138 helps improve rigidity. The bottom 138 of the reinforcement member 136 has a shape making it possible to freely detachably fix the distal cover 110 to the main distal part 109.

Formed on the distal surface of the main distal part 109 is an L-shaped hard hook 140, which is a locking section, having a locking ditch 139 used to freely detachably fix the distal cover 110.

The bottom 138 of the reinforcement member 136 has a hook inserting section 141 in which the hook 140 can be inserted in the axial direction at a certain angle of rotation. Furthermore, on the bottom 138 of the reinforcement member 136, a convex claw 142 directed toward a center of rotation, O, of the distal cover 110 and to be fitted into the locking ditch 139 with a rotation of the distal cover 110 is formed on the margin of the hook inserting section 141.

The whole surface on the distal side of the bottom 138 of the reinforcement member 136 having the hook inserting section 141 is covered by the main distal cover 134.

Next, a procedure for attaching the distal cover 110 to the main distal part 109 will be described.

Figure 19B:
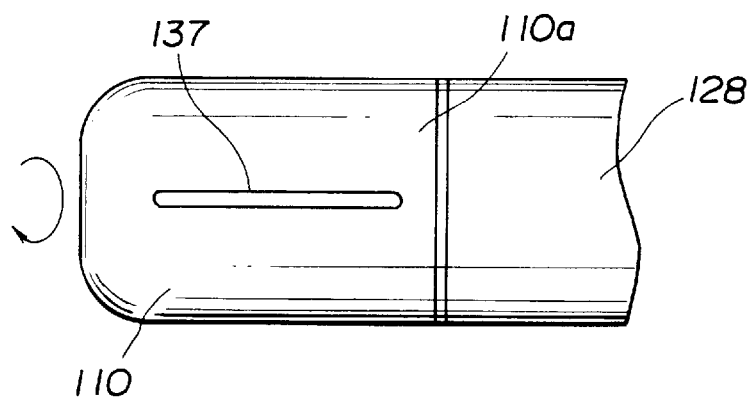
FIG. 19B is a second explanatory diagram for explaining attachment of the main distal part and distal cover shown in FIG. 17.
Figure 21A:
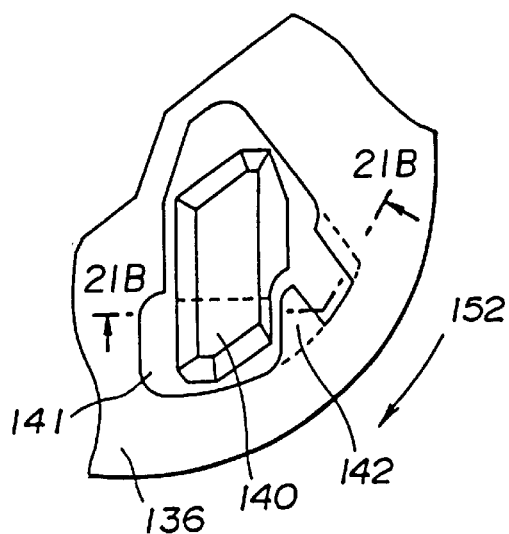
FIG. 21A is a fourth explanatory diagram for explaining attachment of the main distal part and distal cover shown in FIG. 17.

First, as shown in FIG. 19A, while the cover indicator 137 is aligned with the scope indicator 132, the distal cover 110 is inserted in the axial direction of the main distal part 109 at a certain angle of rotation. As shown in FIG. 19B, the distal cover 110 is attached to the main distal part 109. At this time, the presence of the cover indicator 137 and scope indicator 132 assists in recognizing a direction in which the distal cover 110 should be inserted. This results in improved efficiency in attaching or detaching the cover. FIG. 21A is a view showing the state of the distal cover inserted in the axial direction from the distal side.

Figure 21B:
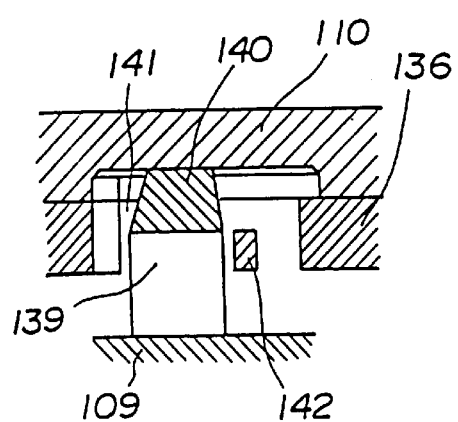
FIG. 21B is a sectional view showing a B—B section of FIG. 21A.
Figure 22:
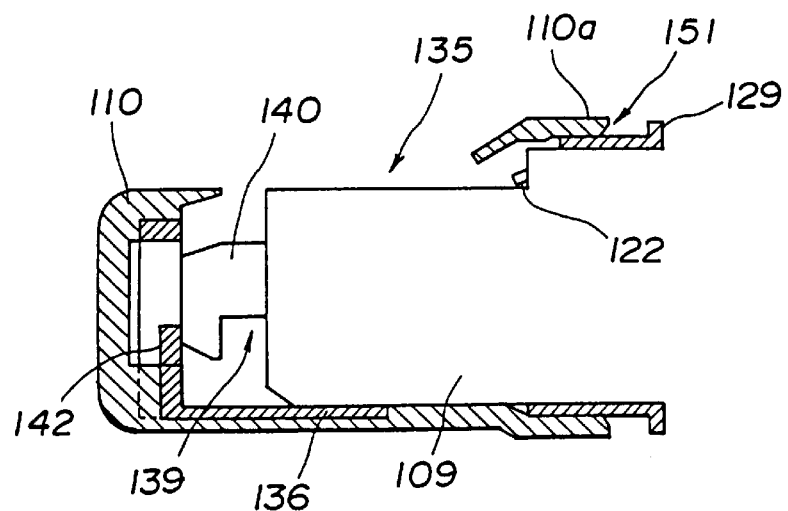

As shown in FIG. 21B that is a B—B sectional view of FIG. 21A, in this state, the hook 140 is stowed in the hook inserting section 141 (the main distal cover is not shown). Since the edge of the distal cover 110 is, as shown in FIG. 22, chamfered 151 over the whole circumference thereof, the distal cover 110 can pass over the main distal part 109 and insulator 129 smoothly without a jerk or the like. Moreover, it can be prevented that the distal cover 110 is turned over at the time of insertion.

Figure 19C:
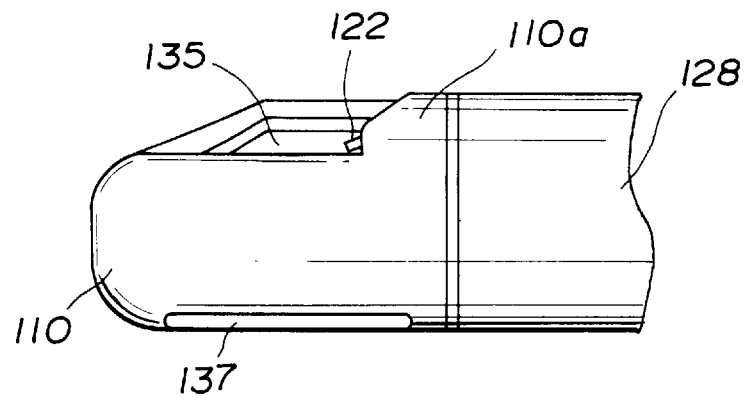
FIG. 19C is a third explanatory diagram for explaining attachment of the main distal part and distal cover shown in FIG. 17.
Figure 23A:
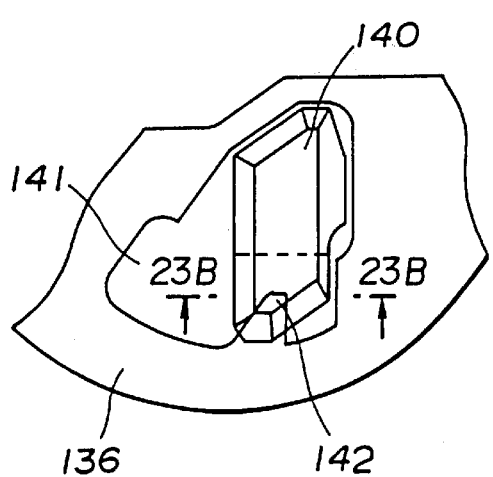
FIG. 23A is a fifth explanatory diagram for explaining attachment of the main distal part and distal cover shown in FIG. 17.
Figure 23B:
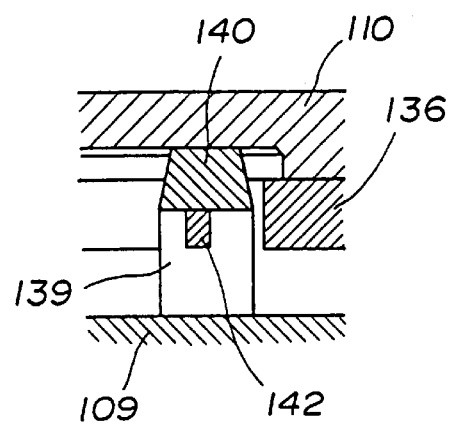
FIG. 23B is a sectional view showing a C—C section of FIG. 23A.

When the distal cover 110 is rotated in a direction of an arrow 152 in FIG. 21A, the state shown in FIG. 23A is set. As shown in FIG. 23B that is a C—C sectional view of FIG. 23A, the claw 142 of the reinforcement member 136 is fitted in the locking ditch 139 of the hook 140, the distal cover 110 will not come off in the axial direction of the main distal part 109 (See FIG. 19C).

The tightening section 110a is, as mentioned above, formed annularly as a proximal portion of the distal cover 110 along the whole circumference of the distal cover 110, the distal cover 110 can be prevented from shifting in the direction of rotation owing to frictional force occurring between the tightening section and insulator 129.

Figure 24A:
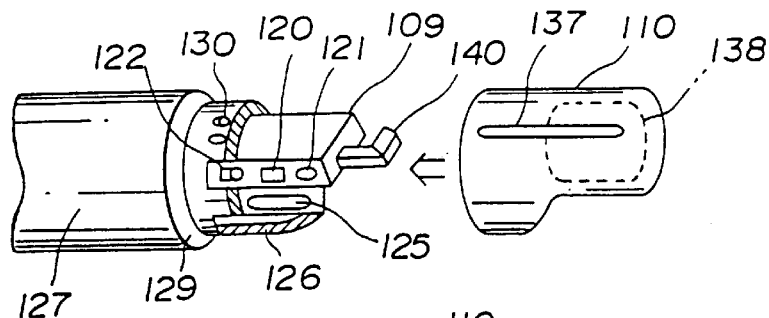
FIG. 24A is a sixth explanatory diagram for explaining attachment of the main distal part and distal cover shown in FIG. 17.

After the distal cover 110 shown in FIG. 24A is attached to the main distal part 109, when the distal cover 110 is rotated, the claw 142 rotates while substantially fitted in the locking ditch 139 of the hook 140. Since the claw 142 or reinforcement member 136, and the hook 140 or main distal part 109 are hard members, frictional force occurring between them is relatively small.

By contrast, the tightening section 110a is an elastic member. Frictional force occurring between the distal cover 110 and insulator 129 during rotation of the distal cover 110 is larger than frictional force occurring between the reinforcement member 136 and main distal part 109.

Figure 24B:
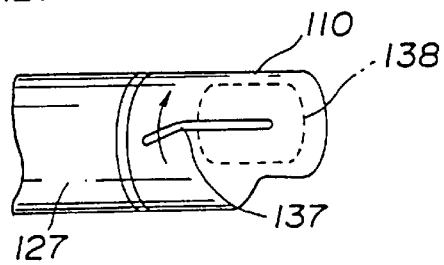
FIG. 24B is a seventh explanatory diagram for explaining attachment of the main distal part and distal cover shown in FIG. 17.

When the distal cover 110 is attached, if a torque is insufficient, as shown in FIG. 24B, the tightening section 110a of the distal cover 110 may not be placed at a given position. In this case, the cover indicator 137 distorts, whereby it can be readily recognized that the distal cover 110 is not attached at a correct position.

Figure 24C:
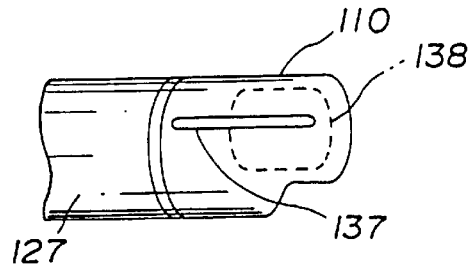
FIG. 24C is a ninth explanatory diagram for explaining attachment of the main distal part and distal cover shown in FIG. 17.

In this case, an area of the distal cover 110 around the tightening section 110a is rotated again until the cover indicator 137 is straightened. The distal cover 110 can then be attached at the given position as shown in FIG. 24C.

For detaching the distal cover 110, the foregoing procedure is reversed. As shown in FIG. 18, for detaching the distal cover 110, the distal cover 110 is rotated to a position indicated with a dotted line in FIG. 18. At this time, the distal cover 110 is rotated by an angle $\theta 1$, and then pulled and detached.

By the way, the range of the field of view of the objective optical system including the objective lens 120 is defined with an angle $\theta 2$ in FIG. 18. When the distal cover 110 is detached from the main distal part 109, the edge of the distal cover 110 enters the range defined with the angle $\theta 2$ without fail.

If the distal cover 110 almost comes off during use, the distal cover 110 enters the field of view without fail. An operator can therefore recognize through an endoscopic image the fact that the distal cover 110 almost comes off.

In this embodiment, the distal cover 110 is inserted relative to the main distal part 109, rotated, and attached thereto. Any other procedure of attachment or detachment will do as long as the distal cover 110 enters the field of view of the objective optical system while coming off.

Even when the distal cover 110 is rotated for attachment or detachment, the therapeutic instrument stand 125 will not interfere with the distal cover 110 within the movable range thereof. This is because the opening 135 is formed and the rotatable range of the distal cover 110 is limited to the range defined with the angle $\theta 1$ shown in FIG. 18. Since the therapeutic instrument stand 125 and distal cover 110 will not interfere with each other, if the distal cover 110 should almost come off, the handling efficiency of the therapeutic instrument stand 125 will not deteriorate.

As described above, according to this embodiment, when the main distal part 109 and distal cover 110 are attached to each other with a rotation, the rotational range of the distal cover 110 is defined with the angle $\theta 1$, while the range of the field of view of the objective optical system including the objective lens 120 is defined with the angle $\theta 2$. When the distal cover 110 comes off from the main distal part 109, the edge of the distal cover 110 enters the range defined with the angle $\theta 2$ without fail. When the distal cover 110 almost comes off during use, the distal cover 110 enters the field of view without fail. An operator can therefore readily recognize through an endoscopic image the fact that the distal cover 110 almost comes off.

Figure 25:
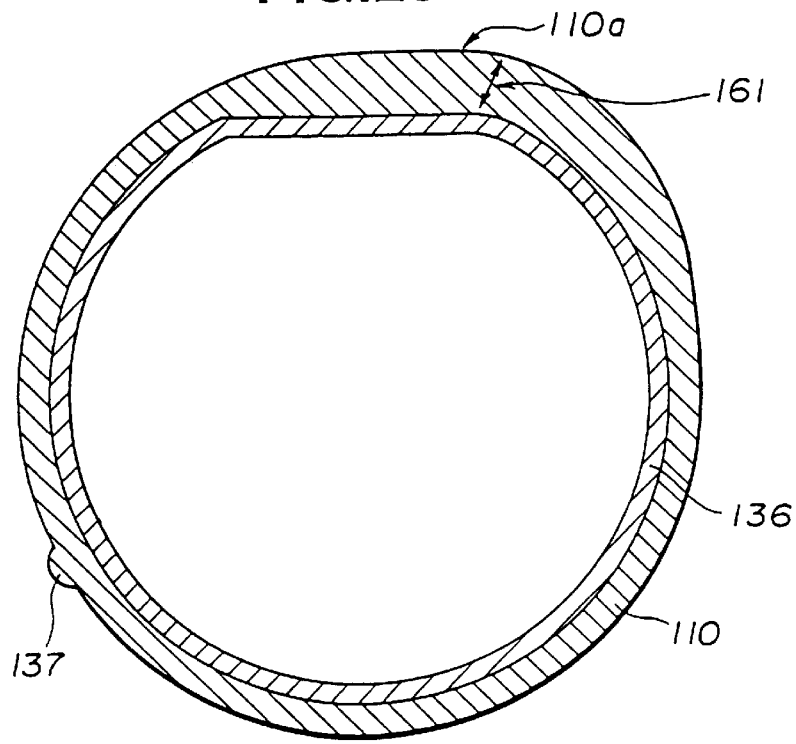

As shown in FIG. 25, the tightening section 110a may be structured to have a thickness that is not uniform over the circumference thereof. In this case, a thick part 161 of the tightening section 110a which has the largest thickness is a portion radially farthest from the center. A larger torque is applied to a portion farther from the center during rotation of the distal cover 110. In this embodiment, when the distal cover 110 is rotated, the largest torque is applied to the thick part 161. Because of the thickness, deformation of the thick part 161 can be prevented.

Figure 26:
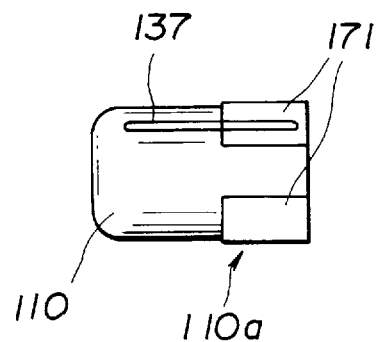

As shown in FIG. 26, ribs 171 may be formed on the edge of the distal cover 110. For attaching or detaching the distal cover 110, the distal cover 110 is rotated by holding the ribs 171. The presence of the ribs 171 enables easy rotation.

Figure 27:
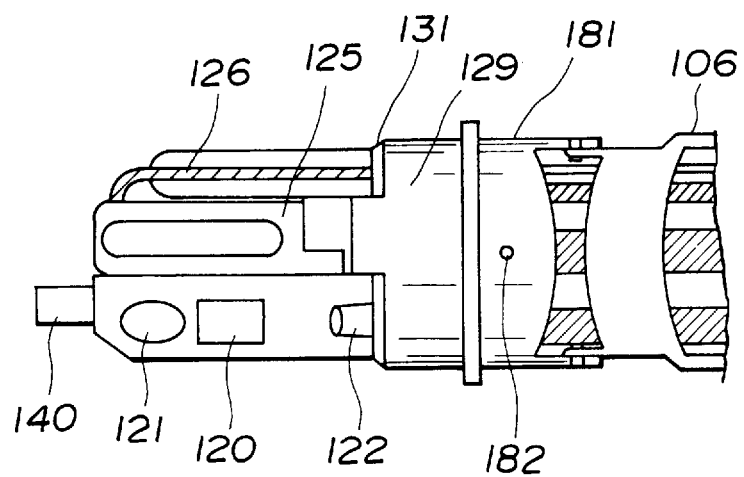

As shown in FIG. 27, an indicator 182 may be formed on the top of a connection tube 181 that is one of the components constituting the bending part 106 connected to the distal part 105 in order to clearly indicate the vertical direction of the bending part 106. In this case, the indicator 182 is formed by boring a round hole in the connection tube 181. A torque is applied to the connection tube 181 during attachment or detachment of the distal cover 110. At this time, stress is converged on the surroundings of the indicator 182. For this reason, the portion of the connection tube 181 having the indicator 182 is designed to have the largest width for the purpose of ensuring strength.

(Fourth Embodiment)

Figure 28:
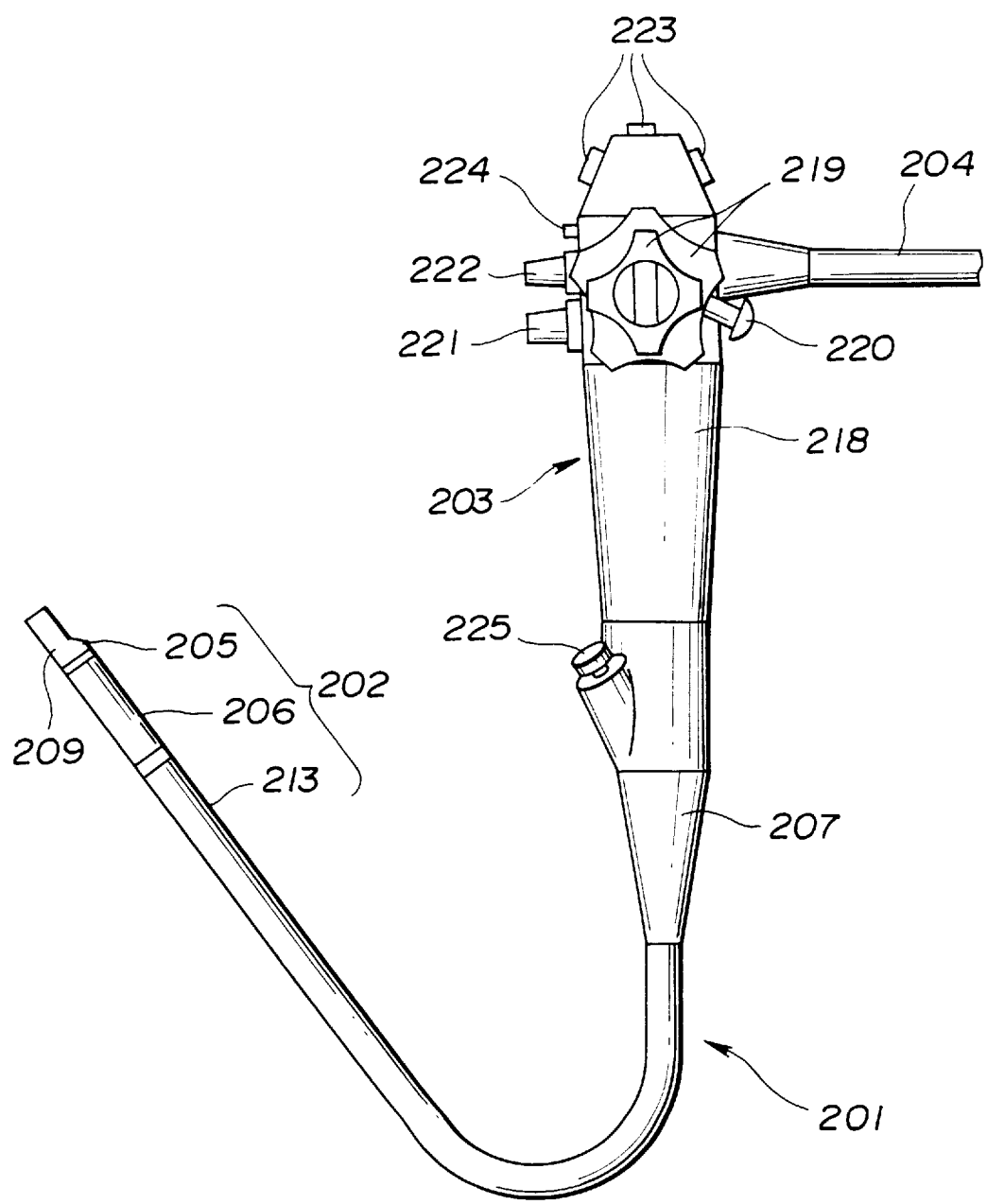
FIGS. 28 to 35 relate to a fourth embodiment of the present invention.

As shown in FIG. 28, an endoscope 201 of the fourth embodiment comprises an elongated insertion unit 202, an operation unit 203 located at the back end of the insertion unit 202, and a universal cord 204 extending laterally from the operation unit 203. The insertion unit 202 has a distal part 205, a bending part 206 capable of bending freely, and an elongated flexible part 213 having flexibility in that order from the distal side. A tapered break prevention section 207 is formed as the proximal portion of the flexible part 213. The operation unit 203 is coupled to the proximal end of the break prevention section 207.

Figure 29:
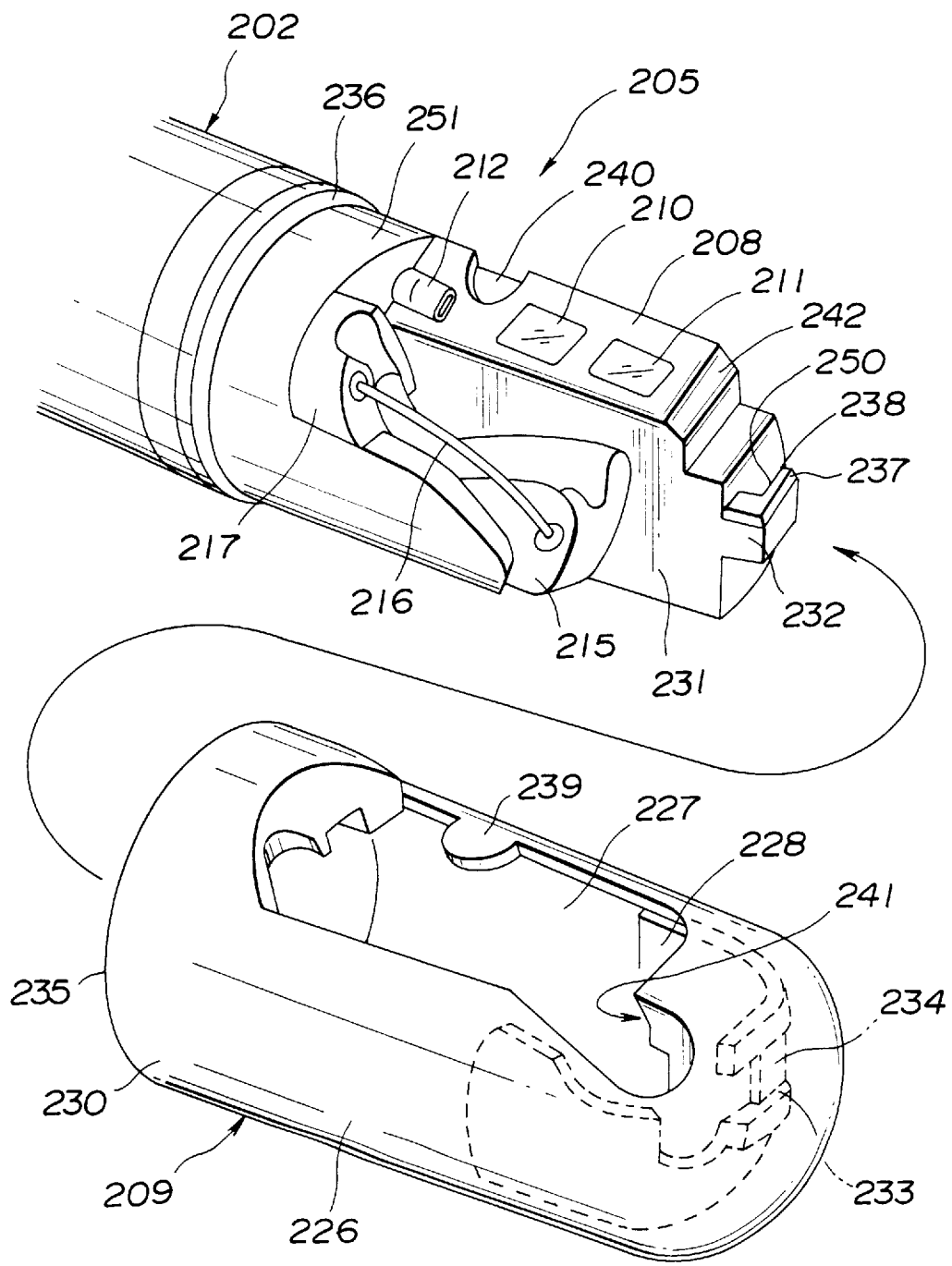

A distal cover 209 is freely detachably attached to a hard main distal part 208 (more particularly, made of a material having rigidity such as stainless steel) constituting the distal part 205. FIG. 29 is a diagram showing the distal part 205 of the insertion unit 202 of the endoscope 201 in enlargement, wherein the distal cover 209 is detached from the main distal part 208.

As shown in FIG. 29, in the main distal part 208, an objective lens 210 whose field of view lies in a direction orthogonal to the axial (longitudinal) direction of the insertion unit 202, and an illumination lens 211 for emitting illumination light in the direction of the field of view for illumination are arranged mutually adjacently in the longitudinal direction. Furthermore, an aeration/perfusion nozzle 212 communicating with an aeration/perfusion channel (not shown) incorporated in the insertion unit 202 is located on the proximal side of the main distal part 208 and directed toward the objective lens 210 for the purpose of supplying a cleaning solvent used to clean the objective lens 210, supplying air used to remove water drops adhering to the objective lens 210, or aerating a body cavity.

An imaging device such as a CCD, which is not shown, is located at the position of the image plane of the objective lens 210. The imaging device photoelectrically converts a formed image, and transmits an image signal resulting from the photoelectric conversion to a video processor or camera control unit connected via the universal cord 204 over a signal cable connected to the imaging device. The video processor or camera control unit carries out signal processing so as to convert the image signal into a standard video signal, and displays an endoscopic image formed by the imaging device on a color monitor that is not shown.

Figure 33:
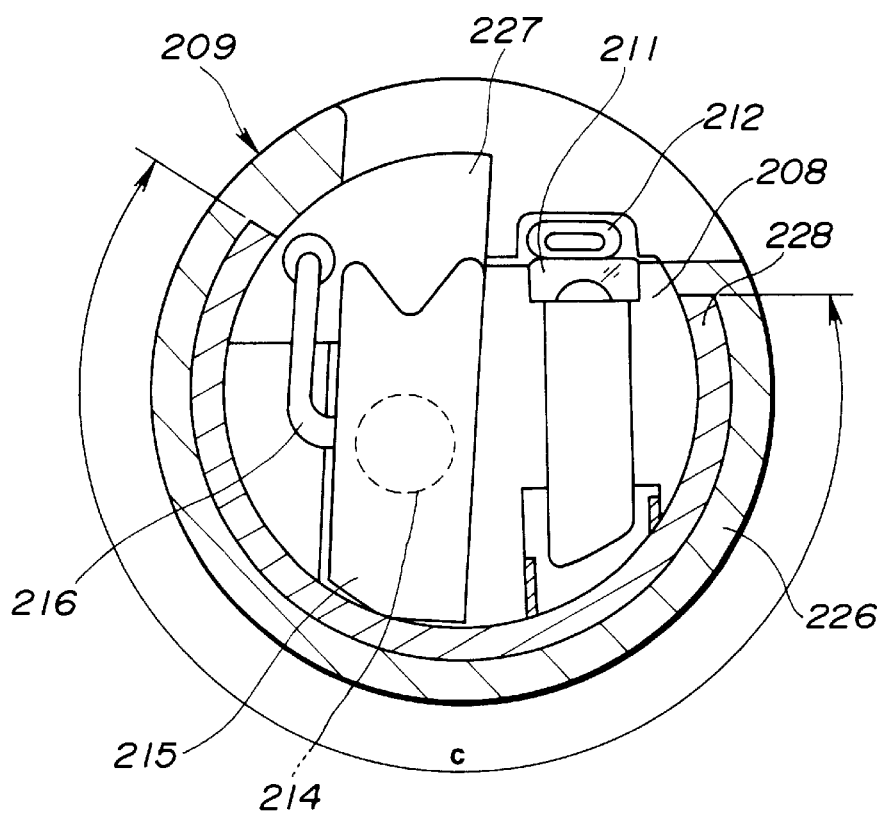

The distal surface of a bundle of light guide fibers is, as shown in FIG. 33, located inside the illumination lens 211 in the main distal part 208. The bundle of light guide fibers runs through the universal cord 204 via the insertion unit 202 and operation unit 203. When a light guide connector attached to the terminal of the bundle of light guide fibers is connected to a light source apparatus that is not shown, illumination light supplied from the light source apparatus is transmitted, and emitted through the distal surface toward the field of view of the objective lens 210 via the illumination lens 211.

The opposite portion of the main distal part 208 adjoining a semi-cylindrical portion having the aeration/perfusion nozzle 212, objective lens 210, and illumination lens 211 is cut out with a lateral fraction alone left intact. In a space 231 created by the cutout (an area of the main distal part 208 near the proximal end thereof), a therapeutic instrument stand 215 is located with the proximal end thereof supported by the main distal part 208. The tip of a standing wire 216 running through the insertion unit 202 is connected to a position near the distal end of the therapeutic instrument stand 215. An area on the distal side of the space 231 is used to attach or detach the distal cover 208 (more particularly, used to tilt the distal cover 208 for attachment or detachment).

A therapeutic instrument channel opening 214 (See FIG. 33) communicating with a therapeutic instrument channel (not shown) incorporated in the insertion unit 202 is formed to be opposed to the therapeutic instrument stand 215 in the main distal part 208. A therapeutic instrument jutting out through the therapeutic instrument channel opening 214, which is not shown, has the direction of jutting thereof restricted depending on the setting of the inclination (standing angle) of the therapeutic instrument stand 215.

The standing wire 216 having one end connected to the therapeutic instrument stand 215 is passed through the insertion unit 202, and connected to a standing mechanism incorporated in the operation unit 203. A therapeutic instrument standing lever 220 is connected to the standing mechanism. By turning the therapeutic instrument standing lever 220, the standing wire 216 is pulled and the inclination of the therapeutic instrument stand 215 is changed. Thus, a direction in which the tip of a therapeutic instrument juts out can be controlled or varied.

For preventing disconnection of a high-frequency knife, an insulation block 217 is embedded in an area of the main distal part 208 adjacent to the therapeutic instrument channel opening 214 and near an area in which the standing wire 216 is located.

As shown in FIG. 28, the operation unit 203 has, in a portion thereof proximal to a grip body 218 to be gripped by a user (upper part of FIG. 28), a bending knob 219 used to bend the bending part 6, a therapeutic instrument standing lever 220, an aeration/perfusion button 221 used for aeration or perfusion, a suction button 222 used for suction, and a plurality of operation switches 223 used to give instructions concerning image control including an instruction instructing display of a still image to the video processor or camera control unit.

The operation unit 203 has a standing wire cleaning base 224 at a position adjacent to the suction button 222. The standing wire cleaning base 224 communicates with the proximal end of a standing wire channel (not shown) through which the standing wire 216 is passed, and is used to clean the standing wire channel. The proximal end of the therapeutic instrument channel incorporated in the insertion unit 202 communicates with a channel insertion port 225. A therapeutic instrument can be inserted through the channel insertion port 225.

As shown in FIG. 29, the main distal cover 226 forming the distal cover 209 is shaped like a cap or a cylinder, of which one end looks like a hemisphere, using an elastic member made of a rubber or the like so that the main distal cover 226 can cover the main distal part 208. The main distal cover 226 has an opening 227 on the side on which the opening 227 coincides with the objective lens 210, illumination lens 211, and therapeutic instrument stand 215.

An insert 228 having a rigid locking section made of stainless steel or hard plastic or the like is formed as part of the main distal cover 226 so that the insert can cover a portion on the distal side of the main distal part 208. A process for forming the insert as part of the main distal cover 226 may be a so-called insert molding process of pouring an elastic member into a die holding the insert 228 during molding, or a process of forming them separately and uniting them using an adhesive or the like.

In this embodiment, as shown in FIG. 29, the rigid insert 228 having a locking concave part 233 (adjoining a locking wall 234) (serving as a locking section) for freely detachably fixing the distal cover 226 to the main distal part 208 is formed inside the distal surface of the main distal cover 226 as part of the main distal cover 226. An L-shaped locking convex part 232 serving as an engaging means, which is engaged with the locking concave part 223 in order to freely detachably attach the distal cover 226, is formed on the distal surface of the rigid main distal part 208. A fixing mechanism enabling attachment or detachment through simple work and permitting firm fixation with high positioning precision is thus realized.

Next, a procedure of attaching the distal cover 209 to the main distal part 208 will be described.

Figure 30:
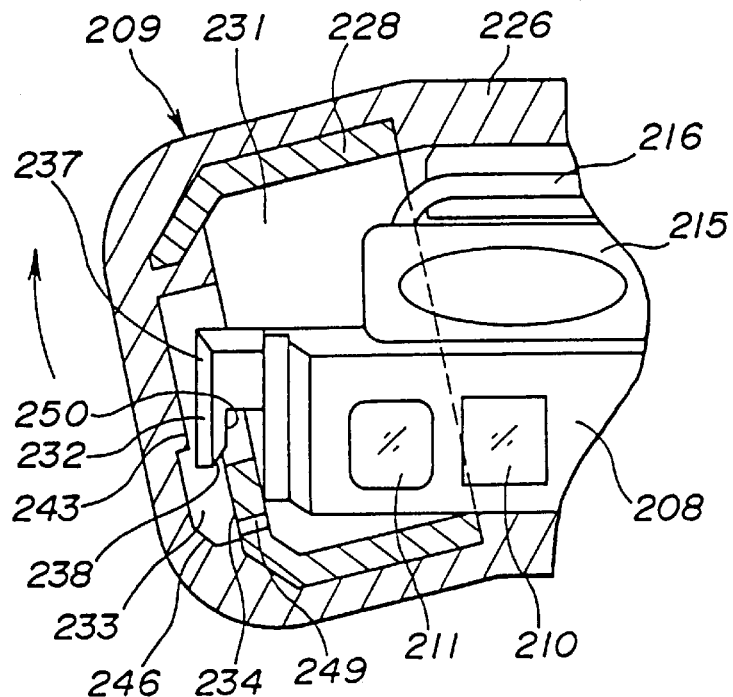

FIG. 30 shows a state in which the distal cover 209 is attached to the main distal part 208 (a partly sectional view).

A tightening section 230 for elastically tightening a close-contact section 251 near the proximal end of the main distal part 208 when annularly placed on the close-contact section 251 is formed as the proximal portion of the distal cover 209. The insert 228 of the distal cover 209 is held from outside with the distal cover 209 put on the main distal part 208. While the space 231 located in front of the therapeutic instrument stand 215 is used to tilt the distal cover 209, the L-shaped locking convex part 232 forming the locking means formed on the distal side of the main distal part 208 is engaged with the locking concave part 233 of the distal cover 209.

Since the locking convex part 232 has a guide surface 237 on the distal side and has an insertion guide surface 238 on the opposite side of the locking convex part 232 relative to the therapeutic instrument stand 215, the guide surfaces assist in engaging the locking convex part 232 with the locking concave part 233 of the distal cover 209.

Figure 31:
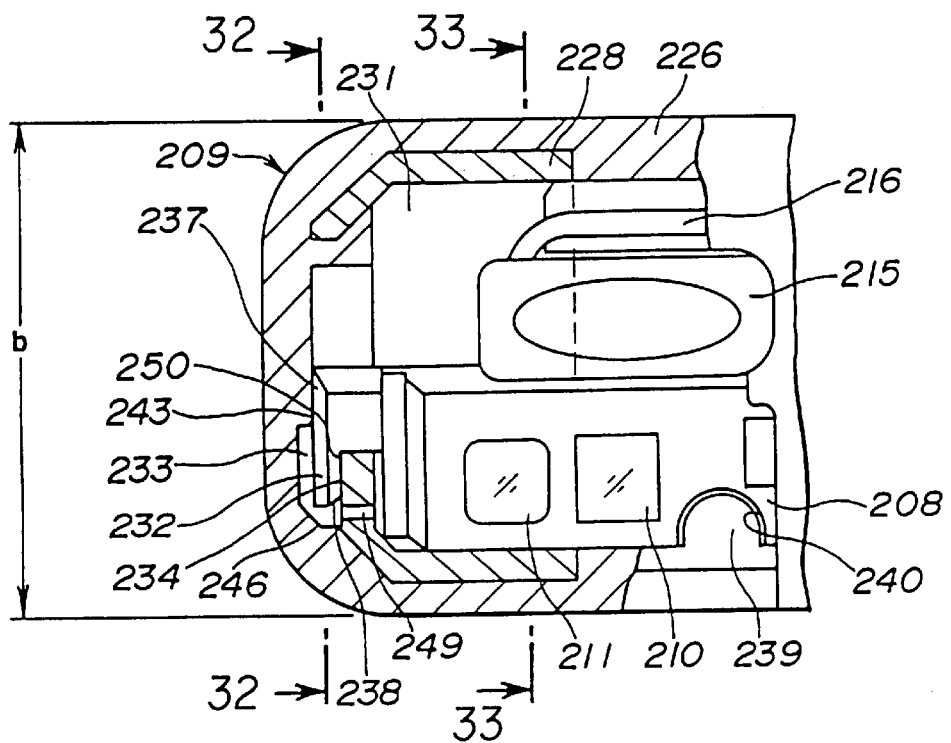

While the distal cover 209 is tilted in a direction of an arrow in FIG. 30, the locking convex part 232 is hung on the locking wall 234 of the distal cover 209. A back end 235 of the distal cover 209 is placed on a stepped abutment surface 236 formed at the proximal end of the main distal part 208. With this work, the work of attaching the distal cover 209 to the main distal part 208 of the endoscope 201 is completed. The state shown in FIG. 31 is attained.

As shown in FIG. 29, a concave part 240 is located behind the objective lens 210 in the main distal part 208. The distal cover 209 has a convex part 239 to be fitted in the concave part 240. When the distal cover 209 is attached to the main distal part 208 as shown in FIG. 31, the convex part 239 of the distal cover 209 is fitted in the concave part 240.

If the distal cover 209 is not attached reliably to the main distal part 208, part of the objective lens 210 is covered by the convex part 239 or part of the field of view of the objective lens is blocked thereby. The convex part 39 therefore appears in an endoscopic image. Consequently, it can be recognized at sight that the distal cover has not been attached reliably.

Another method making it possible to recognize the fact that the distal cover has not been attached reliably may be such that: when the distal cover is not attached reliably, a gap between a cover slope 241 of distal cover 209 and a cover reception slope 242 of the main distal part 208, which are, as shown in FIG. 29, formed in order to diminish a step and gap between the main distal part 208 and distal cover 209 located on the distal side of the illumination lens 211, becomes 1 mm or more so that the gap can be discerned readily.

A portion of the locking concave part 233 of the main distal cover 226 has a convex surface 243 on which the tip of the locking convex part 232 abuts in an attached state. Even when the distal cover 209 is pushed from the distal side, it will not backlash.

Figure 32:
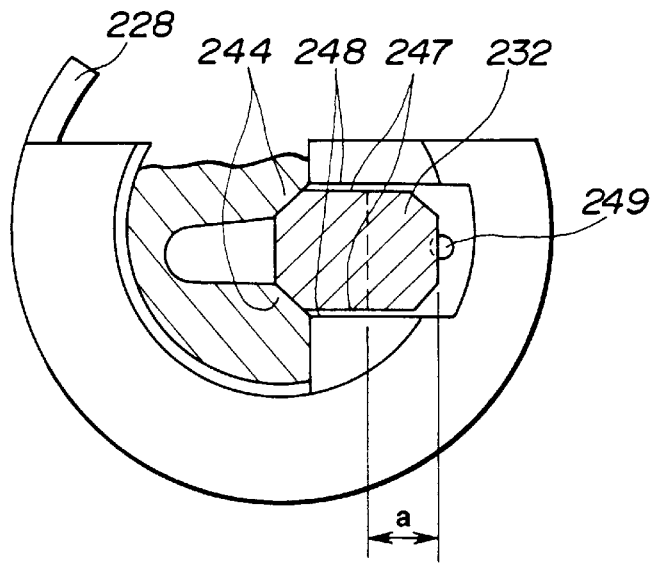

When the distal cover is attached reliably, as shown in FIG. 32 that is an A—A sectional view of FIG. 31, a solid part 244 of the main distal cover 226 adheres closely to the surface of the locking convex part 232 on the side of the therapeutic instrument stand 215. Even when the distal cover 209 receives external force through the therapeutic instrument stand 215, it will hardly come off from the main distal part 208.

The rigid locking convex part 232 and insert 228 are provided with a male engagement section 224 and female engagement section 248 respectively. Since the male so engagement section 247 and female engagement section 248 are engaged with each other, the distal cover will hardly rotate even when receiving external force working in the direction of rotation. When the locking convex part 232 and insert 228 are made of the same material, even if attachment and detachment are repeated, shavings will hardly be created.

The width of the female engagement section 248 of the distal cover 209 of another product is made smaller than that of the male engagement section 247, whereby incorrect attachment is prevented. Furthermore, as shown in FIG. 32, a length corresponding to 5% or more of an external diameter b of the distal cover 209 (See FIG. 31) is preserved as a length a by which the locking convex part 232 and locking wall 234 are engaged with each other. Thus, sufficient engagement strength is ensured.

As shown in FIGS. 30 and 31, a vent 249 is bored in the locking wall 234. After an examination is completed, when the distal cover 209 is detached from the main distal part 208 and cleaned with a cleaning solvent, fluid that has stayed in the locking concave part 233 flows out through the vent 249 and will not remain. When air is supplied through the vent 249 using a syringe or the like, the distal cover 209 will be dried up immediately. The efficiency in cleaning the distal cover 209 thus improves.

A slope 246 that is inclined radially is formed outside the locking concave part 233 in an effort to ensure a large radius for the distal cover 209 along the whole circumference of the distal cover 209 on the distal side thereof and to make the thickness of the main distal cover 206 uniform. Consequently, the slope 246 assists in inserting the endoscope 201 into a body cavity while retaining the strength of the distal cover 209.

The rigid insert 228 formed as part of the distal cover 209 covers, as shown in FIG. 33, at least the opposite side of the therapeutic instrument stand 215 relative to the opening 227. Even when the therapeutic instrument stand 215 is handled to be inverted (or stand) to an excessive degree, since the therapeutic instrument stand 215 hits the rigid insert 228, the therapeutic instrument stand 215 will not be inverted to an excessive degree. It will therefore not take place that the elastic member of the distal cover 209 is damaged.

Even when external force is applied, since the insert 228 acts as a member for protecting the therapeutic instrument stand 215, damaging the therapeutic instrument stand 215 can be prevented. As shown in FIG. 33, a circumferential length c by which the insert 228 engages with the main distal part 208 is larger than a length defined with 180°. Therefore, even when external force is applied radially, since the insert 228 overhangs the main distal part 208, the insert 228, that is, the distal cover 209 will not come off from the main distal part 208.

Figure 34:
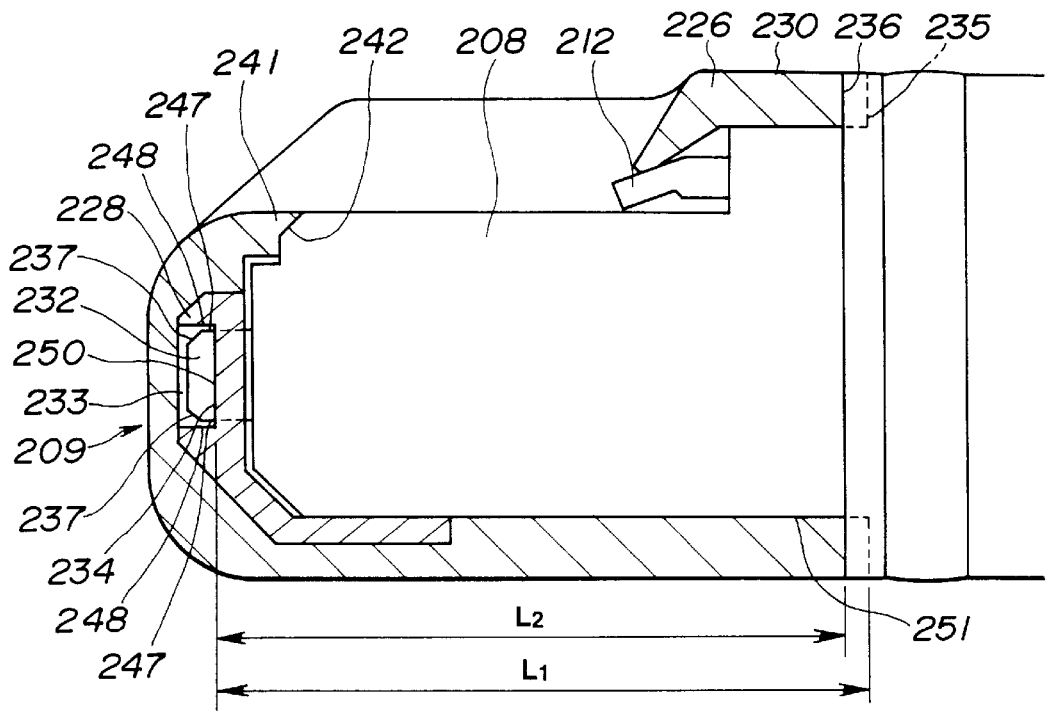

As shown in FIG. 34, a distance in the axial direction between the locking wall 234 and back end 235 of the distal cover 209, L1, and a distance in the axial direction between a hit surface 250 of the locking convex part 232 of the main distal part 208, on which the locking wall 234 abuts, and the abutment surface 236, L2, have a relationship of L1>L2.

In a state in which the distal cover 209 is attached to the main distal part 208, the locking wall 234 of the rigid insert 228 constrains the hit surface 250 of the rigid locking convex part 232 owing to the elastic force of the main distal cover 226 that is formed with an elastic member. The locking wall 234 of the insert 228 will therefore hardly be disengaged from the locking convex part 232 of the main distal part 208.

Figure 35:
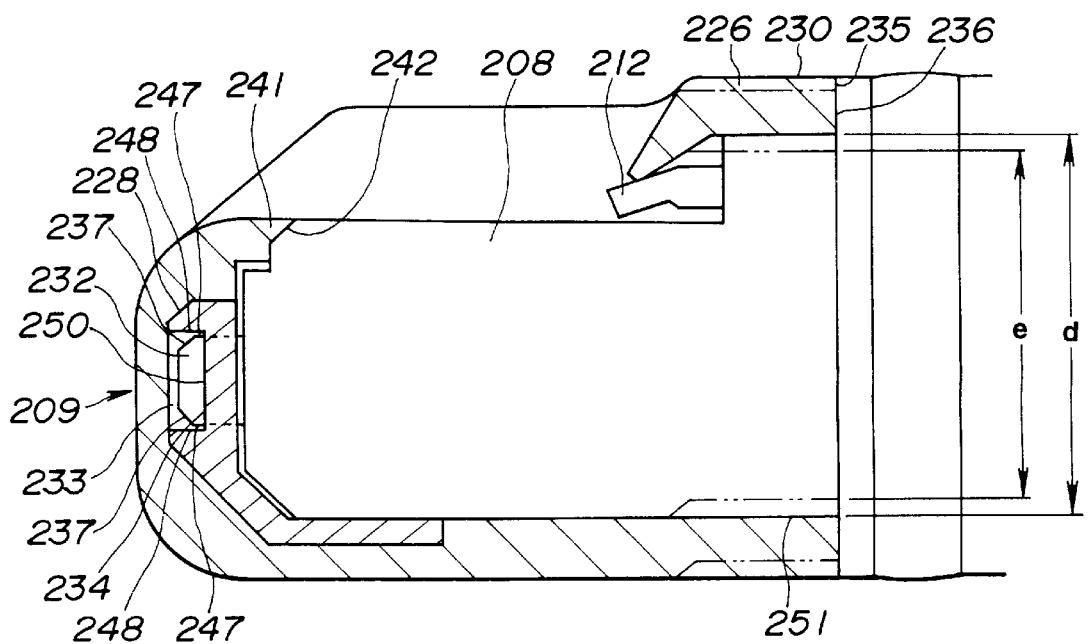

As shown in FIG. 35, the outer diameter of the close-contact section 251 formed as a backward portion of the main distal part 208, d, and the inner diameter of a portion of the tightening section 230 of the distal cover 209 covering the close-contact section, e, has a relationship of d>e. In a state in which the distal cover 209 is attached to the main distal part 208, the close-contact section 251 of the main distal part 208 is tightened with the elastic force exerted by the tightening section 230 of the distal cover 209 formed with an elastic member. The distal cover 209 will therefore hardly come off from the main distal part 208.

Furthermore, the tightening section 230 of the distal cover 209 is a backward portion of the distal cover 209 and is therefore designed so that a quantity of force required for attachment or detachment will not be so large. Alternate long and two short dashes lines in FIGS. 34 and 35 indicate the outline of the distal cover 209 that exists as a unit before attached to the main distal part 208.

The quantity of force required for attaching or detaching the distal cover 209 to or from the main distal part 208 is set to the range from 250 gf to 2000 gf. This results in the distal cover 209 that will therefore hardly drop and enables a user to achieve attachment or detachment with a moderate quantity of force.

The procedure of attaching the distal cover 209 to the main distal part 208 is made uniform among a plurality of endoscopes. A user will therefore not be at a loss when attaching the distal cover 209.

In the endoscope 201 of this embodiment having the aforesaid components, attaching the distal cover 209 can be achieved merely by carrying out the work of tilting the distal cover 209 so as to engage the locking concave part 233 of the rigid insert 228, which is formed as part of the distal cover 209 that is an elastic member, with the L-shaped rigid locking convex part 232 formed on the distal side of the main distal part 208 by utilizing the space 231. The distal cover 209 can be fixed to the main distal part 208 without an additional fixing means such as a screw. This results in simplified work of attachment or detachment. The user-friendly endoscope ensues.

Moreover, it will not take place that the distal cover 209 cannot be attached because a screw or screw fixing jig is missing. Furthermore, since locking the distal cover 209 and main distal part 208 is carried out between rigid members, large fixing force is exerted.

Moreover, the rigid members can be produced more precisely than elastic members. Positioning precision therefore improves. The rigid members will not be displaced or detached during an examination.

Furthermore, as shown in FIG. 32, when the distal cover is attached, the solid part 244 of the main distal cover 226 adheres closely to the surface of the locking convex part 232, which is located on the distal side of the main distal part 208, on the side of the therapeutic instrument stand 215. Besides, as shown in FIG. 34, the distance in the axial direction between the locking wall 234 of the distal cover 209 and the back end 235, L1, and the distance in the axial direction between the hit surface 250, on which the locking wall 234 of the locking convex part 232 of the main distal part 208 abuts, and the abutment surface 236, L2, are set to have the relationship of L1>L2. The locking convex part 232 of the main distal part 208 is therefore constrained with the elastic force of the main distal cover 226 that is an elastic member. This results in intensified locking force.

As shown in FIG. 35, the outer diameter of the close-contact section 251 located as a backward portion of the main distal part 208, d, and the inner diameter of the portion of the tightening section 230 of the distal cover 209 covering the close-contact section 251, e, are set to have the relationship of d>e. In the state in which the distal cover 209 is attached to the main distal part 208, the close-contact section 251 of the main distal cover 208 is tightened with the elastic force of the tightening section 230 of the distal cover 209, which is an elastic member, in an annularly mounted state. This results in the improved ability to prevent drop of the distal cover 209.

Moreover, since the insert 228 having the locking concave part 233 used to freely detachably attach the distal cover 209 to the main distal part 208 is formed inside the distal cover 209 as part of the distal cover 209. Drop of a fixing screw, which often occurs according to the prior art, will therefore not take place.

(Fifth Embodiment)

The fifth embodiment is nearly identical to the fourth embodiment. The same component members are assigned the same reference numerals. The description of the component members will be omitted.

Figure 36:
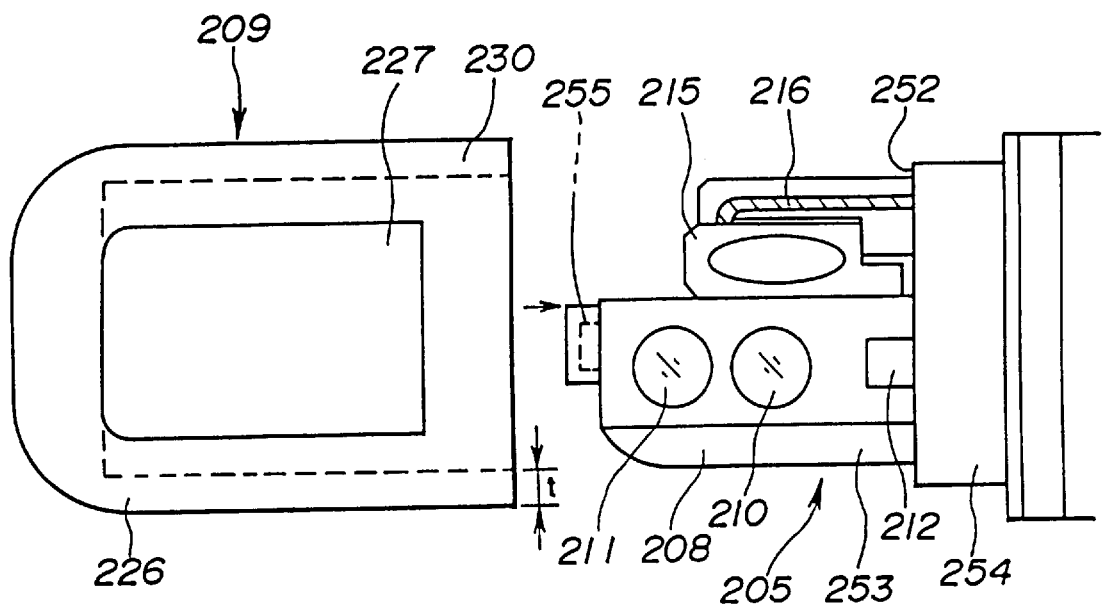
FIGS. 36 to 40 relate to a fifth embodiment of the present invention.
Figure 37:
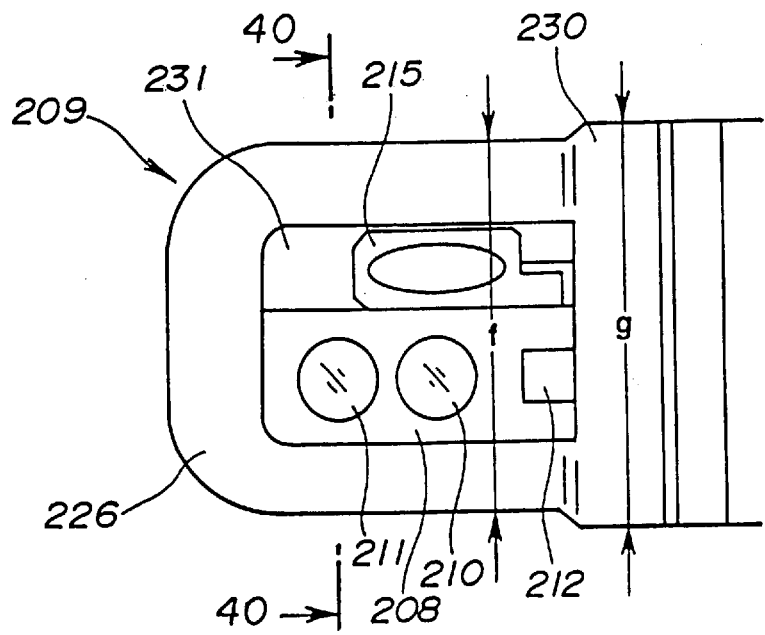

As shown in FIG. 36, the inner diameter of the main distal cover 226, which is an elastic member, of the distal cover 209 is uniform over an area coincident with a forward close-contact section 253 and backward close-contact section 254 of the main distal part 208. The outer diameter and thickness, t, thereof are also uniform. The efficiency in molding the distal cover 209 made of, for example, a rubber is good. A step 252 is located between the forward close-contact section 253 and backward close-contact section 249 of the main distal part 208. When the distal cover 209 is attached, the outer diameters of the areas of the distal cover 209 coincident with the forward close-contact section 253 and backward close-contact section 254 of the main distal part 208, f and g, have a relationship of f<g (See FIG. 37).

At this time, the forward close-contact section 253 and backward close-contact section 249 are tightened by the main distal cover 226 that is an elastic member with large fixing force. Moreover, the tightening ratio of the backward close-contact section 254 is made lower than that of the forward close-contact section 253. This results in the high efficiency in attaching the distal cover 226. Beside, the distal cover 226 will hardly drop.

Figure 38:
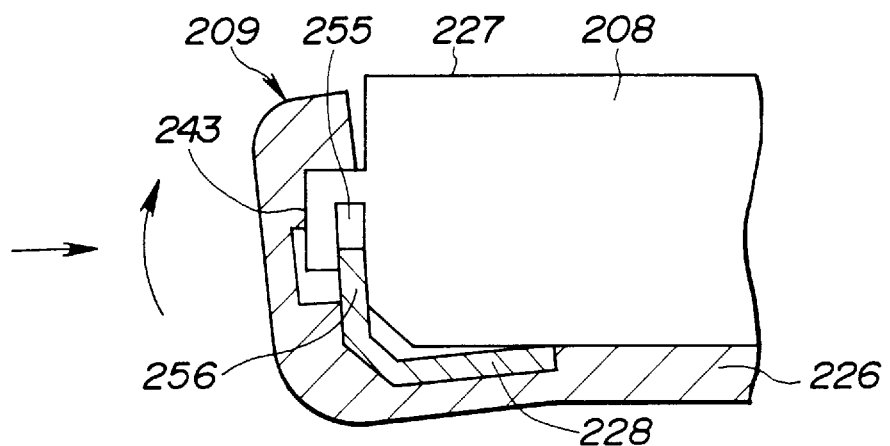
Figure 39:
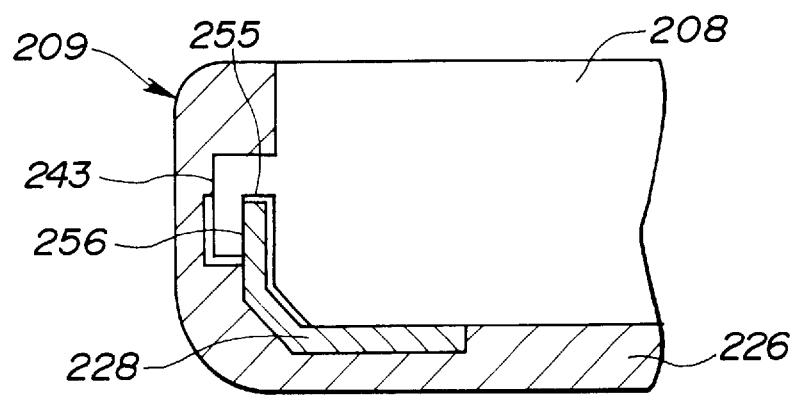

For attaching the distal cover 209 to the main distal part 208, the distal cover 209 is moved in a right-hand direction of an arrow in FIG. 38 by holding the outer surface of the distal cover 209 coincident with the insert 228, so that (the tightening section 230 of) the distal cover 209 can cover the main distal part 208. While the distal cover 209 is tilted in a direction opposite to the opening 227, a rigid locking convex part 256, which is molded as part of the distal cover 209, is fitted in a rigid locking concave part 255 located on the distal side of the main distal part 208. The distal cover 209 is then tilted toward the opening 227 (in a direction of an arc arrow in FIG. 38). Thus, the work of attaching the distal cover 209 to the main distal part 208 of the endoscope 201 in the state shown in FIG. 39 is completed.

Figure 40:
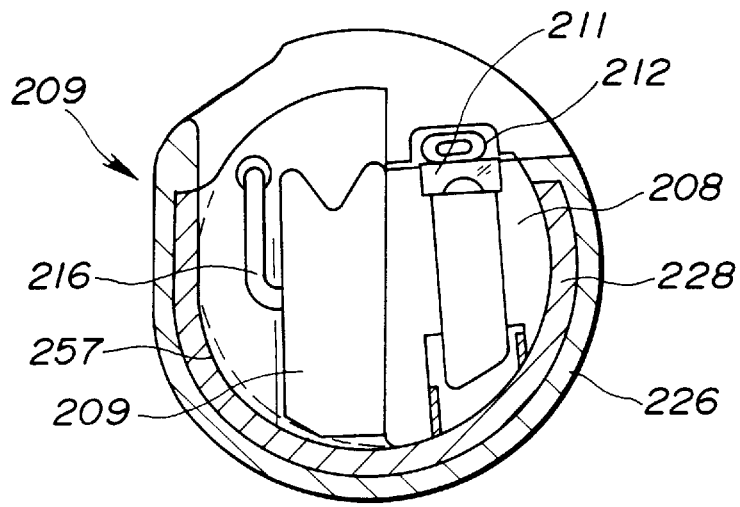

Since the insert 228 of the distal cover 209 is shaped substantially like a semi-circle, it has some degree of elastic force and can therefore be engaged with the main distal part 208. The insert 228 partly has a deformed section 257 (the contour not deformed is indicated with a dashed line in FIG. 40), thus preventing rotation of the main distal part 208 and insert 228. The other components are identical to those in the fourth embodiment.

In the endoscope 201 of this embodiment having the foregoing components, the distal cover 209 can be fixed to the main distal part 208 merely by carrying out the work of tilting the distal cover 209 and fitting the locking convex part 256 of the rigid insert 228, which is formed as part of the distal cover 209 that is an elastic member, into the rigid locking concave part 255 located on the distal side of the main distal part 208 by utilizing the opening 227. Since an additional fixing means such as a screw is unnecessary, the attachment or detachment work is simple. The user-friendly endoscope ensues.

Moreover, it will not take place that since a screw and screw fixing jig are missing, the distal cover 209 cannot be attached. Beside, since locking the distal cover 209 and main distal part 208 is achieved between rigid members, large fixing force can be exerted. The distal cover can be adapted to a main distal part having a small space 231. Moreover, the distal part can be made thinner.

Furthermore, the main distal cover 226, which is an elastic member, of the distal cover 209 tightens the forward close-contact section 253 and backward close-contact section 254. This results in large fixing force.

In FIG. 29 and others, a side-looking endoscope, in which a view direction or the direction of a field of view is a direction orthogonal to the axial direction of an insertion unit, is taken for instance. The forth and fifth embodiments can be adapted to an oblique-looking endoscope in which the direction of a field of view is a forward direction.

(Sixth Embodiment)

Figure 41:
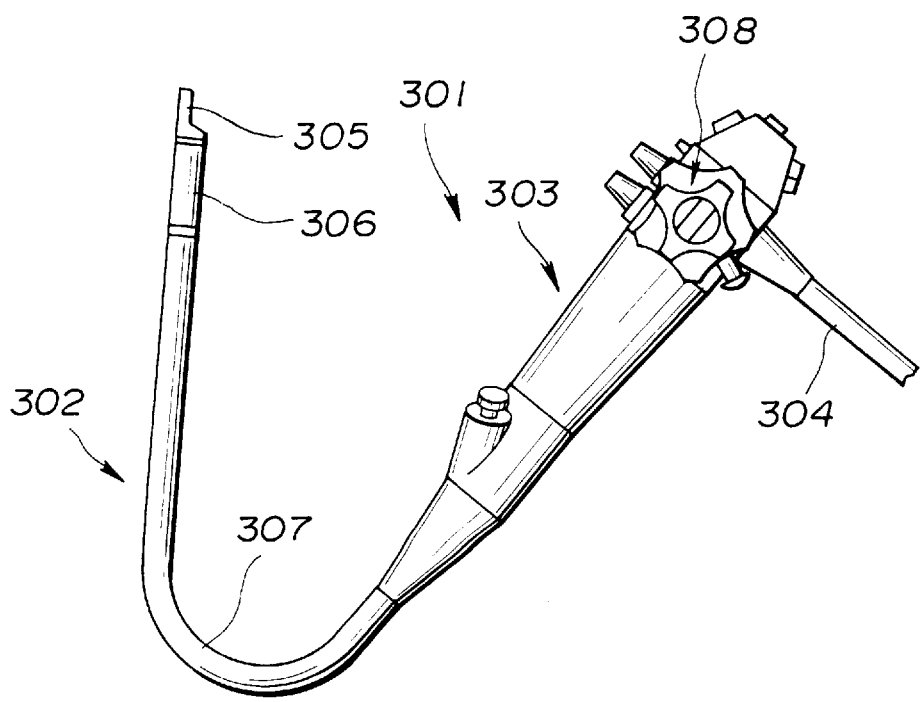
FIGS. 41 to 46 relate to a sixth embodiment of the present invention.

As shown in FIG. 41, an endoscope 301 of this embodiment is, for example, an electronic endoscope consisting mainly of an elongated flexible insertion unit 302, an operation unit 303 located at an end on the operator side of the insertion unit and also serving as a grip to be gripped by the operator, and a universal cord 304 extending from the lateral side of the operation unit 303 and having a connector, which is not shown and connected to a light source apparatus or video processor that is not shown, formed at a tip thereof.

The insertion unit 302 is made by concatenating a distal structure 305, a bending part 306 made by linking a plurality of bending tops and capable of bending vertically and laterally, and a flexible tube 307 having flexibility in that order from the distal side. By handling an operation knob 308 located on the operation unit 303, the bending part 306 is bent and the distal structure 305 is directed in a desired direction.

Figure 42:
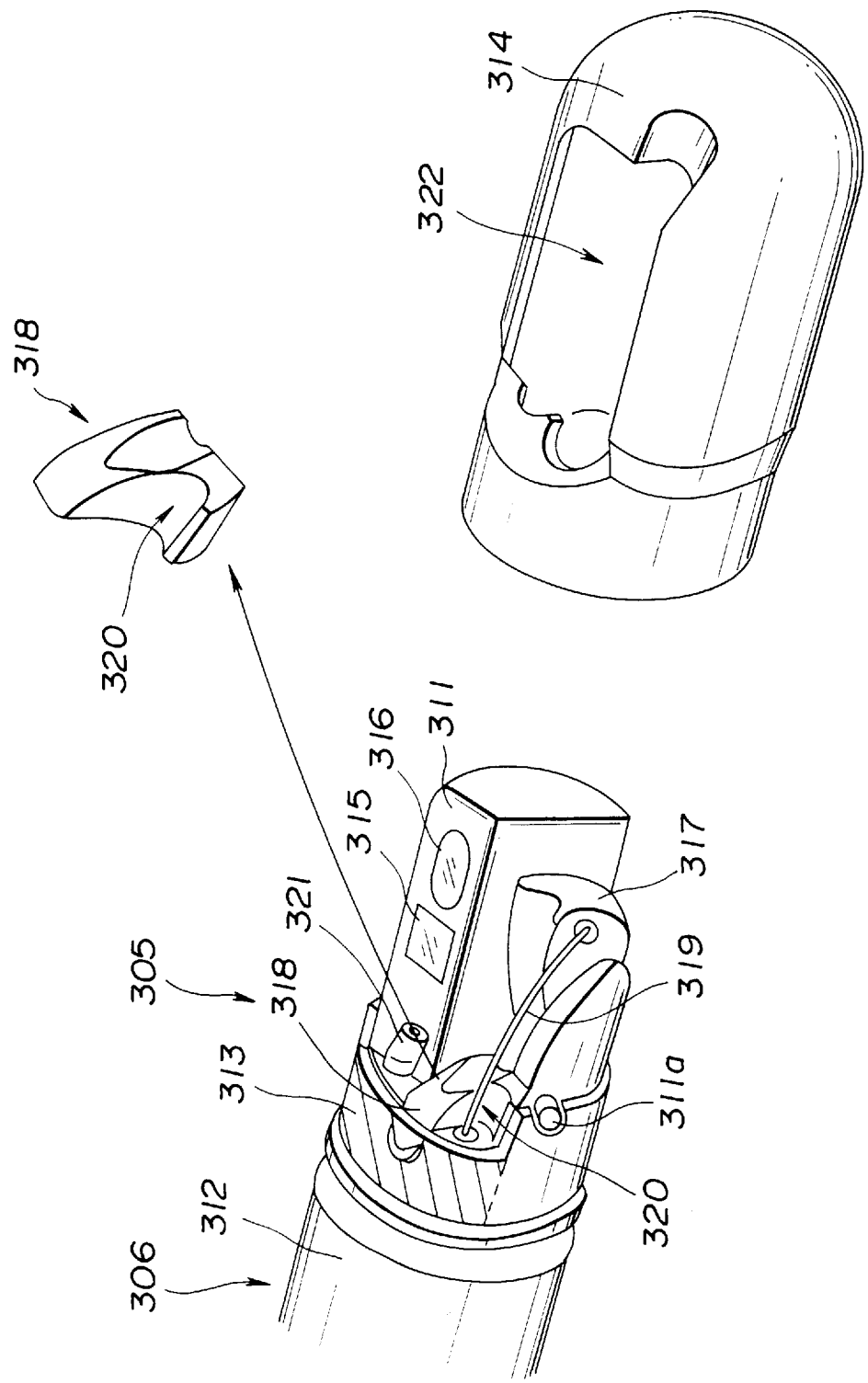

As shown in FIG. 42, the distal structure 305 of the insertion unit 302 is composed mainly of a main distal part 311 made of a metallic material. The proximal end of the main distal part 311 is connected to a bending tube 312 constituting the bending part 306.

An insulator 313 made of a thermoplastic resin such as PSU, a modified PPO, or PEI, or made of an electrically insulating material such as a ceramic or silicon rubber is placed along the outer circumference of a portion of the main distal part 311 connected to the bending tube 312.

A distal cover 314 made of an electrically insulating material in the same manner as the insulator 313 is freely detachably attached to the outer circumference of the main distal part 311.

The distal cover 314 should, preferably, be made of a rubber material, or especially, silicon rubber in consideration of the efficiency in attaching or detaching the distal cover 314 to or from the main distal part 311. When consideration is taken into tear strength, silicon rubber having high tear strength is the most suitable.

For blackening the distal cover 314, ferric oxide (FeO), titanium oxide (TiO2) or powdered carbon manufactured according to a channel method is contained in the material.

An optical system including an objective lens 315 and illumination lens 316 is included in the main distal part 311. Also included is a block member 318 used to avoid contact of a therapeutic instrument with the main distal part 311 occurring when a forceps stand 317 used to direct the therapeutic instrument (not shown) running through the endoscope 310 in a desired direction is directed in the desired direction or when the therapeutic instrument is directed therein using the forceps stand 317.

An end of a forceps standing wire 319 used to rotate the forceps stand 317 with a standing axis (not shown) as a center is fixed to the forceps stand 317. The forceps standing wire 319 is passed through the main distal part 311, bending part 306, and flexible tube 307, and then connected to a forceps standing knob, which is not shown, located on the operation unit 303.

The block member 318 has a forceps standing wire guide ditch 320 that is an opening formed in the direction of the outer circumference of the main distal part 311. The forceps standing wire guide ditch 320 opens in the direction of the outer circumference of the main distal part 311. This results in the improved efficiency in cleaning a portion accommodating the forceps standing wire. 319

A coming-off prevention pin 311a is a metallic pin and fixed to the main distal part 311 at the distal end of the insulator 313 by performing press-fitting, affixing using an adhesive, soldering, or the like.

Also illustrated are a cleaning nozzle 321 used to clean the lens surfaces of the objective lens 315 and illumination lens 316, and a forceps opening 322 created at a position in the main distal part 311 coincident with the forceps stand 317.

Figure 43:
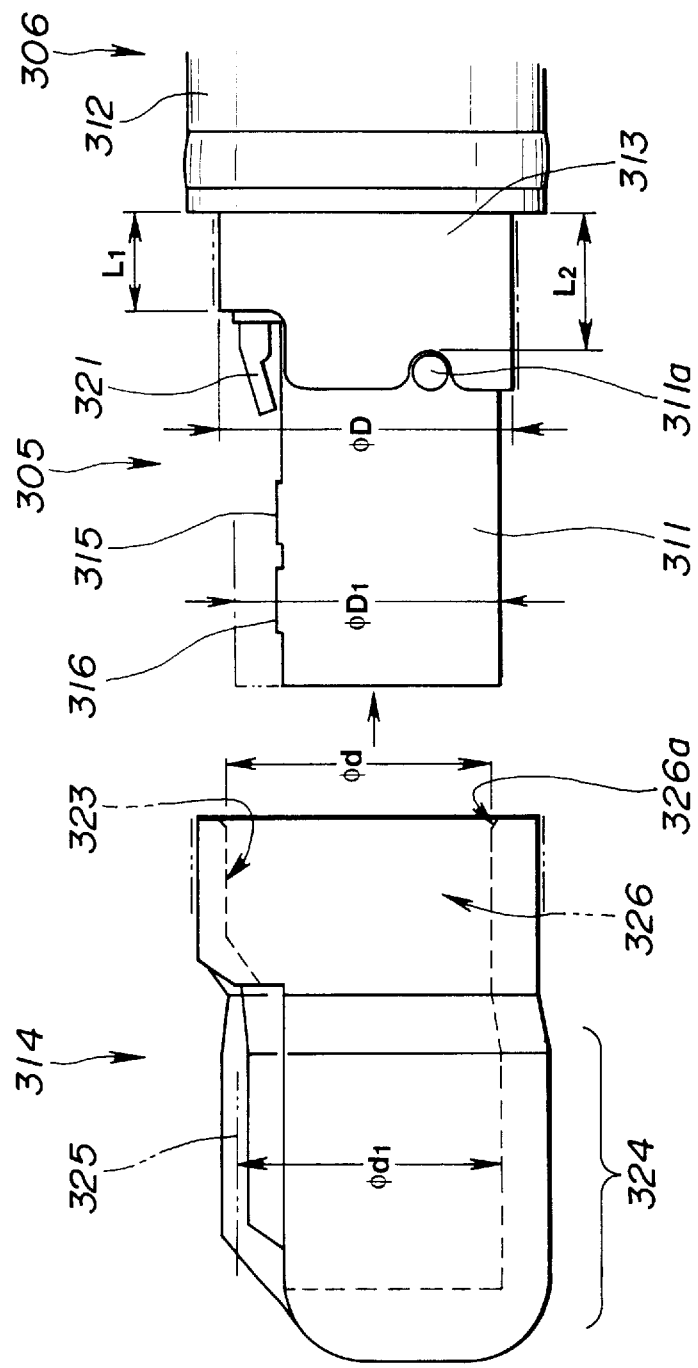

Referring to FIG. 43, the relationship between dimensions of the distal structure 305 will be described.

Figure 44:
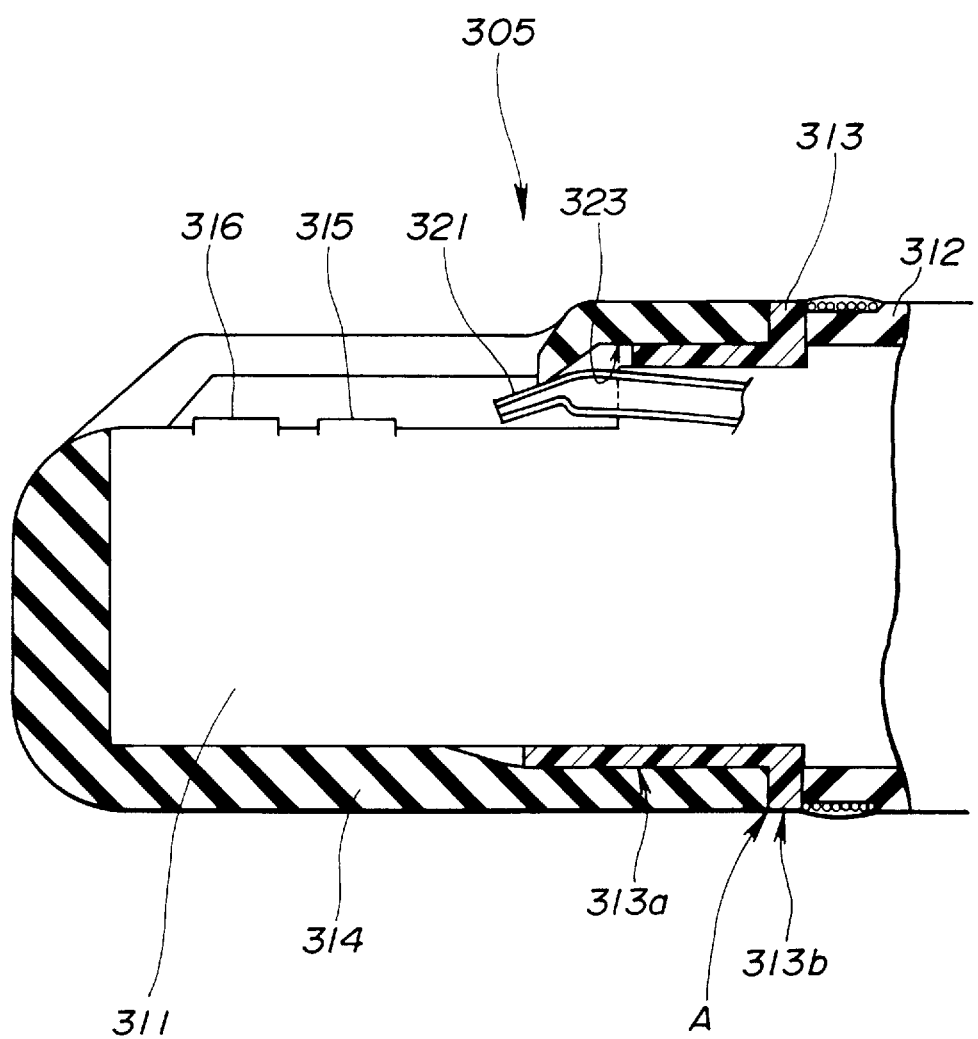

As illustrated, the outer diameter of the insulator 313 placed on the main distal part 311, D, and the inner diameter of an adhering section 323 that adheres to the insulator 313 along the whole outer circumference of the insulator 313, d, have a relationship of $\phi D > \phi d$. When the distal cover 314 is attached to the main distal part 311, they are, as shown in FIG. 44, always attached to each other with the insulator 313, which is an insulating member, in close contact with the adhering section 323 of the distal cover 314.

The value of D/d that is the ratio of the outer diameter of the insulator 313, D, to the inner diameter of the adhering section 323, d is determined so that the fixing strength attained when the adhering section 323 and insulator 313 are in close contact with each other will be 300 gf or larger.

Furthermore, the inner and outer diameters of the adhering section 323 are set to be smaller than those of a distal portion 324 of the distal cover 314. Specifically, assuming that the outer diameter of the main distal part 311 drawn as a cylinder with an alternate long and two short dashes line in FIG. 43 is $\phi D1$, and the inner diameter of a main distal part attachment section 325 of the distal cover 314 which is attached to the main distal part 311 and is drawn as a circle with an alternate long and two short dashes line in FIG. 43 is $\phi d1$, the ratio of D1 to d1 (D1/d1) and the ratio of D to d (D/d) are set to have a relationship of (D/d)>(D1/d1). Thus, the tightening ratio of the distal cover on the operator side and the tightening ratio of the other part thereof are made mutually different.

A slope 326a for facilitating attachment to the insulator 313 is formed on the lateral margin of a space 326 of the adhering section 323 along the inner circumference thereof.

As mentioned above, the outer diameter of the insulator placed on the main distal part, D, and the inner diameter of the adhering section of the distal cover, d, has the relationship of $\phi D > \phi d$. Consequently, when the distal cover is attached to the main distal part, the insulator that is an insulating member and the adhering section of the distal cover can always be brought into close contact with each other.

Moreover, since the outer diameter of the insulator, D, and the inner diameter of the adhering section of the distal cover, d, are set to have the relationship of $\phi D > \phi d$, if at least one of the insulator on the main distal part and the distal cover is made of a rubber material such as silicon rubber, the magnitude of a close contact between the insulator and the adhering section of the distal cover can be increased drastically.

Furthermore, when the value of D/d is set appropriately by changing the values of the inner diameter of the adhering section, d, and of the outer diameter of the insulator, D, the fixing strength attained when the adhering section and insulator come into close contact with each other can be set freely.

When the tightening ratio of the portion on the operator side of the distal cover, which adheres closely to the main distal part along the whole circumference of the distal cover, is set to be higher than that of the other portion thereof, the fixing strength can be improved without a deterioration in attachment ability.

Figure 45:
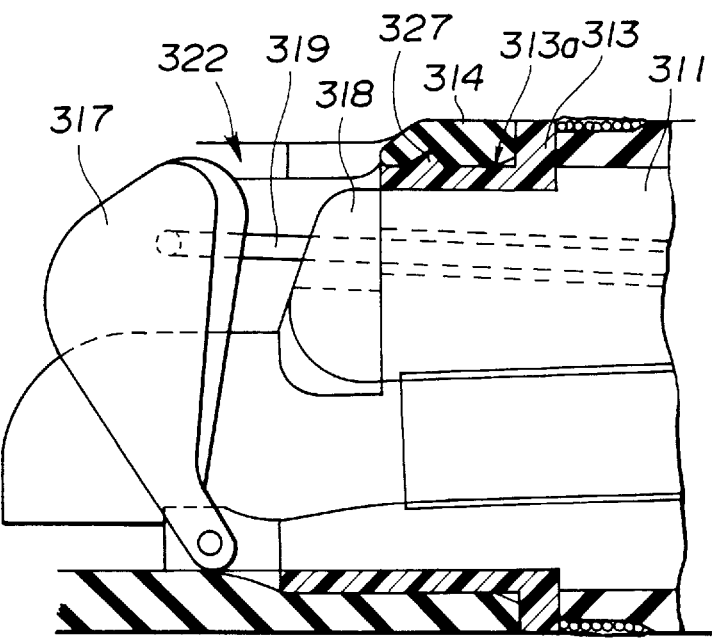

As shown in FIG. 45, a straight portion 313a with which the insulator 313 engages is provided with a convex part 327 that is convex in the outer circumferential direction. Thus, when the distal cover 314 is attached to the main distal part 311, the convex part 327 is thrust into the distal cover 314. Consequently, the fixing strength at which the distal cover 314 is fixed to the insulator 313 on the main distal part 311 can be set higher.

Figure 46:
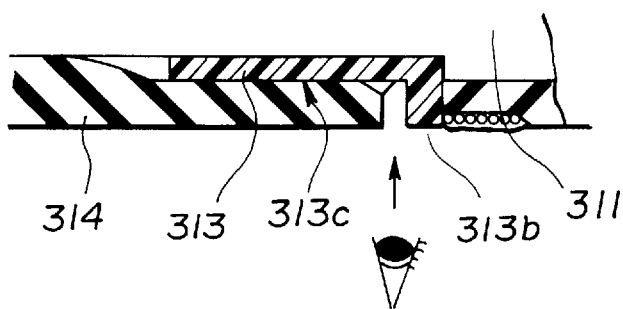

As shown in FIG. 46, an outer circumferential surface 313b and engaging surface 313c of the insulator 313 are colored mutually differently, and the engaging surface 313c and the outer surface of the distal cover 314 are colored mutually differently. The distal cover 314 and the outer circumferential surface 313b may have the same color. When the color of the engaging surface 313c of the insulator 313 is thus made different from the colors of the distal cover 314 and of the outer circumferential surface 313b of the insulator 313, if the attached state of the distal cover 314 to the main distal part 311 is imperfect, a user can recognize by visually checking differences in color the fact that the attachment of the distal cover to the main distal part is imperfect. Thus, imperfect attachment of the distal cover to the main distal part can be prevented reliably. Leakage of a high-frequency current caused by the imperfect attachment can be prevented.

Furthermore, in this embodiment, the endoscope is an electronic endoscope. The present invention is not limited to the electronic endoscope, but may, needless to say, apply to a fiberscope or a direct-looking endoscope other than the side-looking endoscope employed in this embodiment.

The present inventor made studies on a necessary width in the axial direction by which insulating members should come into close contact with each other (hereinafter, creepage distance) for the purpose of preventing a high-frequency current from leaking out to the outer circumferential surface of a distal structure when a high-frequency therapeutic instrument is used in combination with the above endoscope. The procedure adopted by the present inventor will be described below.

Specifically, a high-frequency current and high-frequency therapeutic instrument which are generally used are employed, and an output of a power source is 100 W. The tip of the endoscope is moistened with physiological saline, and the high-frequency therapeutic instrument is inserted into the forceps channel in the endoscope and stationed in the distal part of the endoscope. Under two conditions in which the high-frequency therapeutic instrument is in contact with the metallic portion of the main distal part of the endoscope and is not in contact therewith, the high-frequency current is allowed to conduct, and a leakage current is measured at position A in FIG. 44 at which the distal cover 314 hits the insulator 313. The measurement was carried out repeatedly by setting the creepage distance to several values.

The results of the measurements will be described with reference to Table 1.

TABLE 1

| Creepage distance | In contact | Not in contact |
|---|---|---|
| 2.05 | Current leaks out. | No current leaks out. |
| 2.10 | " | " |
| 2.15 | " | " |
| 2.35 | No current leaks out. | " |
| 2.50 | " | " |
| 2.65 | " | " |

As seen from Table 1, when the creepage distance is 2.35 mm, no leakage current flows irrespective of the contact state or non-contact state. This means that when the creepage distance is set to 2.5 mm or larger, no leakage current will occur. In this embodiment, therefore, the creepage distance (L2 in FIG. 43) between electrically insulating materials, that is, the insulator on the main distal part and the distal cover is set to 2.5 mm or larger.

There is a problem that when the creepage distance is increased in order to prevent leakage of a high-frequency current, the distal structure becomes longer. There is therefore a demand for a structure capable of preventing leakage of a high-frequency current and making the distal structure as short as possible. In this embodiment, when a high-frequency therapeutic instrument is used to conduct an endoscopic treatment, if the outer surface of the distal part of the endoscope in the direction of a field of view (in a direction in which forceps jut out) and an intracavitary wall get so close to each other as to nearly touch each other, the high-frequency therapeutic instrument cannot be jutted out from the forceps channel. Consequently, a high-frequency treatment cannot be conducted. Moreover, a high-frequency treatment is not conducted until it is checked through an endoscopic image if the distance between an intracavitary wall in the direction of the field of view and the outer surface of the distal part of the endoscope is sufficient.

As shown in FIG. 43, the creepage distance of the insulator 313 in the direction of the field of view, L1, is set to be smaller than the creepage distance of the insulator 313 in a direction opposite to the direction of the field of view, L2, on the assumption that the outer surface in the direction of the field of view can be reliably separated from the intracavitary wall. In other words, the creepage distance in the direction of the field of view, L1, and the creepage distance in a direction opposite to the direction of the field of view, L2, has a relationship of L2>L1.

Since the creepage distance in the direction of the field of view, in which it can be seen clearly if the insulator is approached to an intracavitary wall, and the creepage distance in a direction opposite to the direction of the field of view, L1 and L2, are thus set to have the relationship of L2>L1, the risk of leakage of a high-frequency current can be avoided and the distal structure can be designed shorter in length. When the creepage distance on the side of the field of view is made smaller than that on the back side, safety against a leakage current can be guaranteed satisfactorily.

Figure 47:
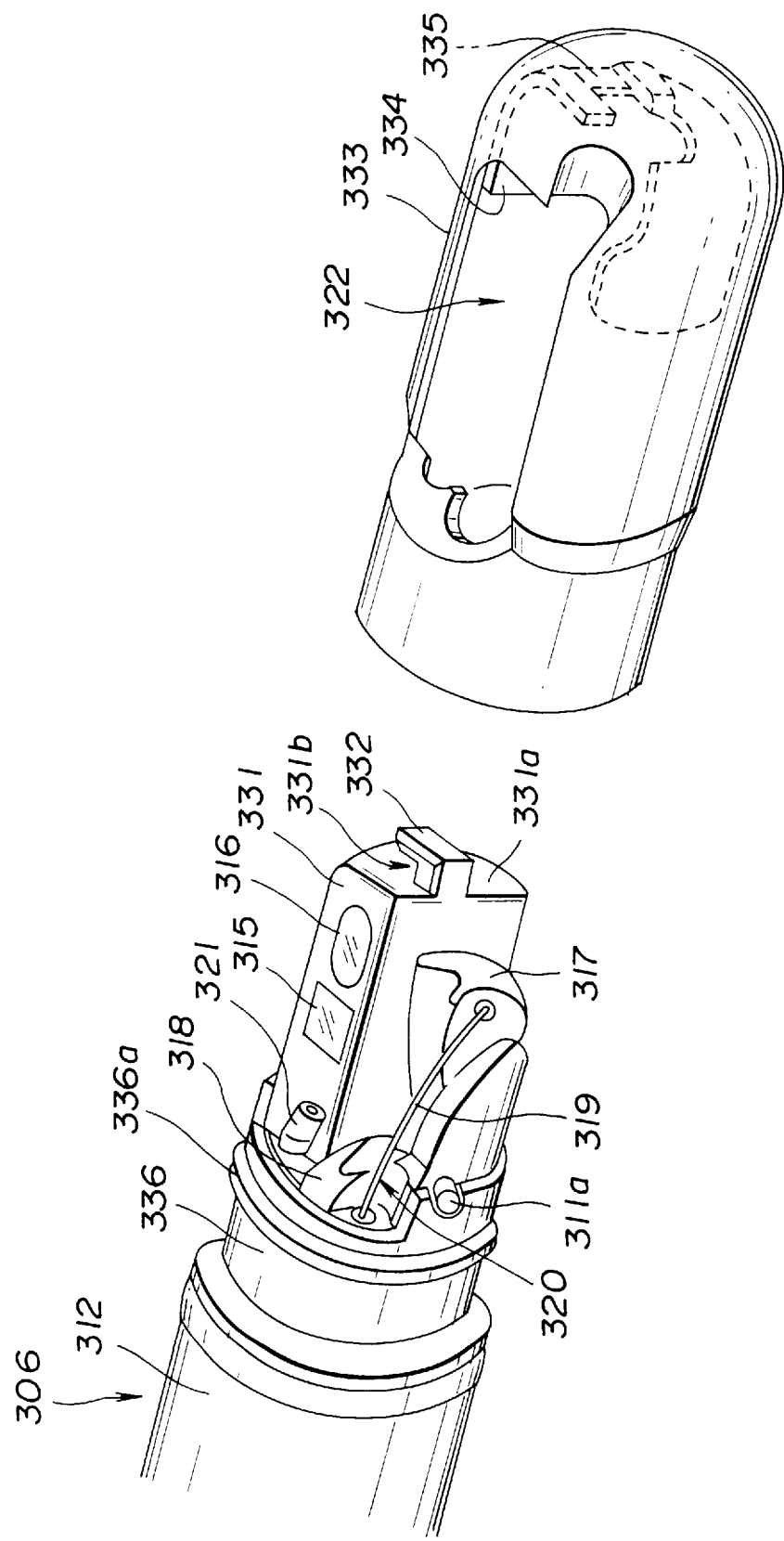
FIGS. 47 to 50 relate to a sixth embodiment.

In a variant of this embodiment, as shown in FIG. 47, a substantially L-shaped fixing section 332 is formed on the distal surface of the main distal part 331 of this embodiment, and a convex part 336a is formed at least part of the outer circumference of the insulator 336 placed on the main distal part 331. A reinforcement member 334, and a fitted section 335 into which the fixing section 332 of the main distal part 331 is fitted are formed along the inner circumference of the distal cover 333 to be attached to the main distal part 331. The other components are identical to those of the aforesaid embodiment. The same members are assigned the same reference numerals. The description of the members will be omitted.

Figure 48:
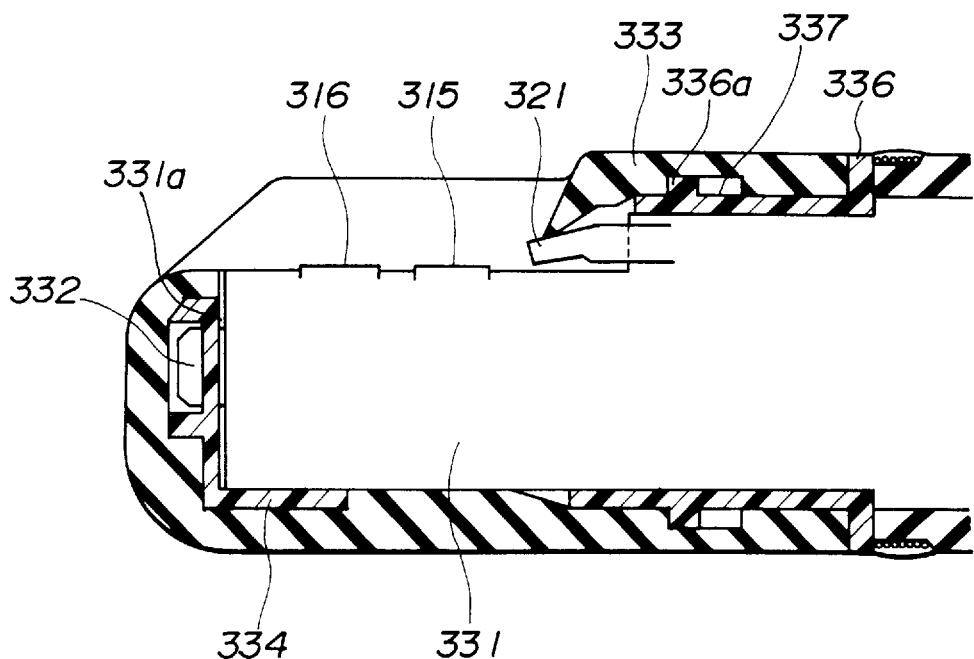

The distal cover 333 is attached to the main distal part 331 as shown in FIG. 48. The fitted section 335 is placed in a space 331b defined between the fixing section 332 and the distal surface 3331a of the main distal part, whereby the distal cover 333 is attached to the main distal part 331. At this time, the convex part 336a of the insulator 336 is fitted in a groove 337 dug along the inner circumference of the distal cover 333.

Figure 49:
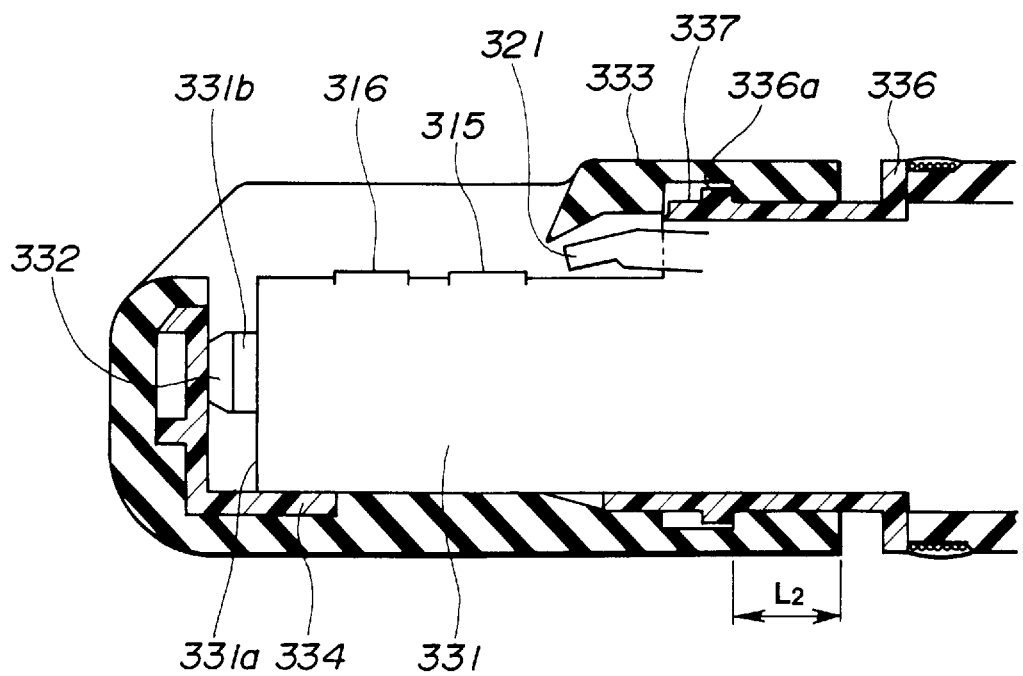

In this embodiment, the dimensions of parts including the convex part 336a and groove 337 are set so that if an imperfectly attached state should be attained because the fixing section 332 hits the reinforcement member 334 as shown in FIG. 49, the convex part 336a will be fitted in the groove 337, then the distal cover 33 will be attached to the main distal part 331, and eventually the creepage distance between insulating members in a direction opposite to the direction of the field of view, L2, will be 2.5 mm or larger. Thus, safety against a leakage current is guaranteed.

Figure 50:
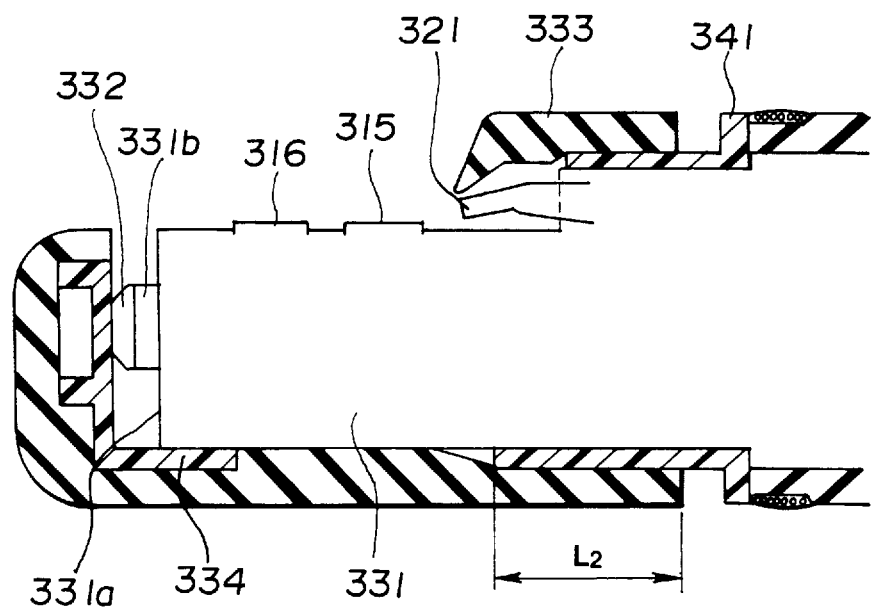
Figure 51:
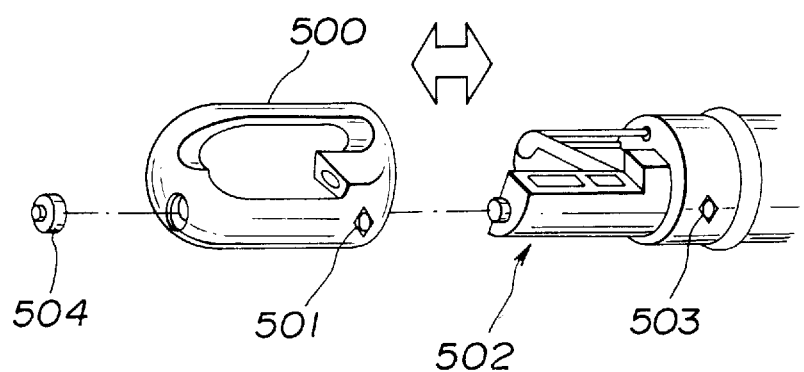
FIG. 51 is a diagram showing the structures of a main distal part and distal cover in accordance with a prior art.

Even when the insulator 341 does not have the convex part like the one shown in FIG. 50, the dimensions of parts should merely be set so that if an imperfectly attached state is attained because the fixing section 332 hits the reinforcement member 334, the creepage distance between insulating members in a direction opposite to the direction of the field of view, L2, will be 2.5 mm or larger. Thus, safety against a leakage current can be guaranteed.

Embodiments formed by combining parts of the aforesaid embodiments also belong to the present invention.

In the present invention, it will be apparent that a wide range of different embodiments can be formed on the basis of the invention without a departure from the spirit and scope of the invention. This invention will be limited to the appended claims but not re restricted to any specific embodiment.

What is claimed is:

1. An endoscope having a distal cover any one of freely attachable and detachable to and from, respectively, a distal part of an insertion unit to be inserted into a body cavity for producing optical images of a region of view, said endoscope comprising:

said distal cover is an elastic member which has a rigid locking section; and a main distal part of said distal part of said insertion unit has a rigid locking means for freely detachably being locked in said locking section, wherein a distal surface of said locking means is constrained to move in an axial direction by means of part of said elastic member of said distal cover, with said distal cover being attached to said distal part.

2. The endoscope according to claim 1, wherein said locking section is located on a distal side in said distal cover.

3. The endoscope according to claim 2, wherein the outer diameter of a backward engaged section of said main distal part, with which said distal cover is engaged annularly along the whole circumference thereof, is larger than the inner diameter of a portion of said distal cover to be mated with said engaged section.

4. The endoscope according to claim 1, wherein said locking means is an engaging means for engaging with said locking section with a thrust in said axial direction of said distal cover, in which said insertion unit is inserted longitudinally, and with a rotation, and said distal cover has a constraining means for constraining said distal surface of said locking means to move in said axial direction within at least part of a range of rotation of said distal cover.

5. The endoscope according to claim 1, wherein a distance in said axial direction between a locking surface of said locking section and a back end surface of said distal cover, L1, and a distance in said axial direction between a locking surface of said locking means and an abutment surface on a proximal side of said main distal part, on which said back end surface of said distal cover abuts, L2, has a relationship of L1>L2.

6. The endoscope according to claim 1, wherein a distance in said axial direction between a locking surface of said locking section and a back end surface of said distal cover, L1, and a distance in said axial direction between a locking surface of said locking means and an abutment surface on a proximal side of said main distal part, on which said back end surface of said distal cover abuts, L2, has a relationship of L1>L2.

7. An endoscope having a distal cover freely attachable or detachable to or from a distal part of an insertion unit to be inserted into a body cavity for producing optical images of a region of view, said endoscope characterized in that:

said distal cover that is an elastic member has a rigid locking section;

a main distal part of said distal part of said insertion unit has a rigid locking means to be freely detachably locked in said locking section;

said locking means is an engaging means that is engaged with said locking section with a thrust in the axial direction of said distal cover, in which said insertion unit is inserted longitudinally, and with a rotation; and said distal cover has a constraining means for constraining the distal surface of said locking means to move in the axial direction within at least part of the range of the rotation of said distal cover.

8. An endoscope according to claim 7, wherein with said engaging means set in a state in which the rotation of said distal cover is started, an angle at which said distal cover and main distal part are in contact with each other exceeds 180° around an axis of center of the rotation.

9. An endoscope according to claim 7, wherein said constraining means constrains said distal surface of said locking means to move in the axial direction with said distal cover attached to said main distal part.

10. An endoscope according to claim 7, wherein with said engaging means set in a state in which the rotation of said distal cover is started, a clearance in the direction of rotation between said locking means and locking section is larger than a clearance preserved when said distal cover is attached to said main distal part after the rotation of said distal cover.

11. An endoscope according to claim 7, wherein the largest cross-section of said locking means which is vertical to the axial direction is contained in a cross-section of said main distal part which is vertical to the axial direction.

12. An endoscope according to claim 7, wherein said constraining means constrains the distal surface of said locking means to move in the axial direction using the elastic force of said distal cover that is an elastic member.

13. An endoscope according to claim 7, wherein for attaching or detaching said distal cover to or from said locking means, said distal cover is rotated in a reciprocatory fashion by a given angle about the axial direction of said main distal part.

14. An endoscope according to claim 13, wherein when said distal cover is detached from said locking means, at least part of said distal cover enters the field of view of a viewing optical system located in said distal part of said insertion unit.

15. An endoscope according to claim 7, wherein said endoscope is a side-looking endoscope.

16. An endoscope according to claim 7, wherein said distal cover is formed with an elastic member made of a rubber or thermoplastic elastomer.

17. An endoscope according to claim 7, wherein:

said distal cover includes a single-material section made of one elastic material and defining the contour of said distal cover, and an insert that is a hard member extending in the axial direction of said distal cover, in which said distal cover is attached or detached, within said distal cover; and said single-material section extends in the axial direction of said distal cover, in which said distal cover is attached or detached, beyond said insert.

18. An endoscope according to claim 17, wherein when said distal cover is detached from said locking means, at least part of said distal cover enters the field of view of a viewing optical system located in said distal part of said insertion unit.

19. The endoscope according to claim 7, wherein said locking section is located on a distal side in said distal cover.

20. The endoscope according to claim 19, wherein the outer diameter of a backward engaged section of said main distal part, with which said distal cover is engaged annularly along the whole circumference thereof, is larger than the inner diameter of a portion of said distal cover to be mated with said engaged section.

21. The endoscope according to claim 7, wherein a distal surface of said locking means is constrained to move in an axial direction by means of part of said elastic member of said distal cover at a time of attachment.

22. An endoscope having a distal cover to be freely detachably attached to a distal part of an insertion unit to be inserted into a body cavity for producing optical images of a region of view, said endoscope comprising:

a substantially straight indicator extending parallel to an axial direction of said distal cover, in which said distal cover is any one of attached and detached, is formed on an outer surface of said distal cover, wherein said distal cover includes a single-material section made of one elastic material and defining a contour of said distal cover, and an insert that is a hard member extending in said axial direction of said distal cover, in which said distal cover is any one of attached and detached, within said distal cover, said single-material section extending in said axial direction, in which said distal cover is any one of attached and detached, beyond said insert, and wherein said substantially straigt indicator is formed over said single-material section through the lateral surface of said insert.

23. The endoscope according to claim 22, wherein said distal cover is formed with an elastic member made of any one of a rubber and a thermoplastic elastomer.

24. The endoscope according to claim 22, wherein said hard member is made of any one of a metal and a hard plastic.

25. An endoscope having a distal cover made of an electrically insulating material, and any one of attachable and detachable to and from, respectively, a distal part of an insertion unit to be inserted into a body cavity for producing optical images of a region of view, said endoscope comprising:

said distal cover is an elastic member which has a rigid locking section;

a main distal part of said distal part of said insertion unit has a rigid locking means for freely detachably locked in said locking section;

a portion on a distal side of said main distal part is made of a metal, and said outer surface, on a proximal side thereof, is made of an electrically insulating material;

said distal cover is freely detachably attached to said main distal part;

when said distal cover is attached to said main distal part, part of an inner circumference of said distal cover and part of said outer surface on said proximal side of said main distal part come into close contact with each other along an entire circumferences thereof; and wherein a width, at least in an axial direction opposite to a direction of a field of view, by which a part of said distal cover and a part of said outer surface on said proximal side of said main distal part are brought into close contact with each other, is at least 2.5 mm.

26. The endoscope according to claim 25, wherein a tightening ratio of a first portion of said distal cover, which comes into contact with part of said outer surface on said proximal side of said main distal part along said entire circumference thereof, is set to be larger than a tightening ratio of a second portion thereof.

27. The endoscope according to claim 25, wherein a color of a fitted surface on said proximal side of said main distal part on which said distal cover is fitted is different from colors of said outer surface of said distal cover and of an outer circumference on said proximal side.

28. The endoscope according to claim 25, wherein said endoscope is a side-looking endoscope.

* * * * *